US011298471B2

(12) United States Patent
Caspers et al.

(10) Patent No.: US 11,298,471 B2
(45) Date of Patent: Apr. 12, 2022

(54) LIMITING LIFE TIME OF DISPENSE ASSEMBLY

(71) Applicant: Sanofi-Aventis Deutschland GmbH, Frankfurt am Main (DE)

(72) Inventors: Michael Caspers, Frankfurt am Main, DE (US); Ilona Eggert, Frankfurt am Main, DE (US)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 313 days.

(21) Appl. No.: 16/401,007

(22) Filed: May 1, 2019

(65) Prior Publication Data

US 2019/0247592 A1 Aug. 15, 2019

Related U.S. Application Data

(63) Continuation of application No. 14/373,088, filed as application No. PCT/EP2013/051901 on Jan. 31, 2013, now Pat. No. 10,293,119.

(30) Foreign Application Priority Data

Jan. 31, 2012 (EP) ..................................... 12153382

(51) Int. Cl.
*A61M 5/50* (2006.01)
*A61M 5/20* (2006.01)
(Continued)

(52) U.S. Cl.
CPC .......... *A61M 5/5086* (2013.01); *A61M 5/172* (2013.01); *A61M 5/20* (2013.01);
(Continued)

(58) Field of Classification Search
CPC ............ A61M 2205/14; A61M 5/5086; A61M 5/172; A61M 5/50; A61M 5/19;
(Continued)

(56) References Cited

U.S. PATENT DOCUMENTS

| 533,575 A | 2/1895 | Wilkens |
| 4,915,695 A * | 4/1990 | Koobs ................... A61M 5/315 222/137 |

(Continued)

FOREIGN PATENT DOCUMENTS

| CN | 102202703 A | 9/2011 |
| CN | 102256644 A | 11/2011 |

(Continued)

OTHER PUBLICATIONS

Chinese Office Action for Application No. 201380016252.7, dated Jan. 29, 2016, translation.

(Continued)

*Primary Examiner* — Nathan R Price
*Assistant Examiner* — Melissa A Snyder
(74) *Attorney, Agent, or Firm* — McCarter & English, LLP

(57) ABSTRACT

The technical problem of the present invention to provide a medical device, which exhibits an increased safety of the device and facilitates a safe use is solved by medical device for delivering at least one drug agent, comprising a sensor, a control unit and an attachable dispense assembly, wherein the sensor is configured to detect attachment of the dispense assembly to the medical device, wherein the control unit is configured to determine at least based on a signal from the sensor whether the end of life of the dispense assembly is reached and wherein the medical device is configured to indicate the end of life of the dispense assembly. The technical problem is further solved by a method according to the invention.

12 Claims, 17 Drawing Sheets

Specification includes a Sequence Listing.

(51) Int. Cl.
*A61M 5/24* (2006.01)
*A61M 5/34* (2006.01)
*A61M 5/172* (2006.01)

(52) U.S. Cl.
CPC ............ *A61M 5/2448* (2013.01); *A61M 5/34* (2013.01); *A61M 5/50* (2013.01); *A61M 2205/12* (2013.01); *A61M 2205/14* (2013.01); *A61M 2205/18* (2013.01); *A61M 2205/273* (2013.01); *A61M 2205/276* (2013.01); *A61M 2205/3306* (2013.01); *A61M 2205/507* (2013.01); *A61M 2205/52* (2013.01)

(58) Field of Classification Search
CPC ...... A61M 2205/60; A61M 2205/6063; A61M 2205/6072
See application file for complete search history.

(56) References Cited

U.S. PATENT DOCUMENTS

| | | | |
|---|---|---|---|
| 5,226,895 A | 7/1993 | Harris | |
| 5,279,586 A | 1/1994 | Balkwill | |
| 5,304,152 A | 4/1994 | Sams | |
| 5,320,609 A | 6/1994 | Haber et al. | |
| 5,383,865 A | 1/1995 | Michel | |
| 5,437,635 A * | 8/1995 | Fields | A61M 5/16813 604/65 |
| 5,480,387 A | 1/1996 | Gabriel et al. | |
| 5,505,704 A | 4/1996 | Pawelka et al. | |
| 5,582,598 A | 12/1996 | Chanoch | |
| 5,626,566 A | 5/1997 | Petersen et al. | |
| 5,674,204 A | 10/1997 | Chanoch | |
| 5,688,251 A | 11/1997 | Chanoch | |
| 5,921,966 A | 7/1999 | Bendek et al. | |
| 5,961,495 A | 10/1999 | Walters et al. | |
| 6,004,297 A | 12/1999 | Steenfeldt-Jensen et al. | |
| 6,193,698 B1 | 2/2001 | Kirchhofer et al. | |
| 6,221,046 B1 | 4/2001 | Burroughs et al. | |
| 6,235,004 B1 | 5/2001 | Steenfeldt-Jensen et al. | |
| 6,248,095 B1 | 6/2001 | Giambattista et al. | |
| 6,899,698 B2 | 5/2005 | Sams | |
| 6,936,032 B1 | 8/2005 | Bush, Jr. et al. | |
| 7,241,278 B2 | 7/2007 | Moller | |
| 7,704,231 B2 * | 4/2010 | Pongpairochana | A61M 5/34 604/134 |
| 7,871,397 B2 | 1/2011 | Schraga | |
| 8,674,656 B2 | 3/2014 | Iio et al. | |
| 9,155,835 B2 | 10/2015 | Watanabe et al. | |
| 2002/0052578 A1 | 5/2002 | Moller | |
| 2002/0120235 A1 | 8/2002 | Enggaard | |
| 2003/0050609 A1 | 3/2003 | Sams | |
| 2003/0163089 A1 * | 8/2003 | Bynum | A61M 5/14566 604/154 |
| 2004/0059299 A1 | 3/2004 | Moller | |
| 2004/0210199 A1 | 10/2004 | Atterbury et al. | |
| 2004/0267207 A1 | 12/2004 | Veasey et al. | |
| 2005/0113765 A1 | 5/2005 | Veasey et al. | |
| 2006/0153693 A1 | 7/2006 | Fiechter et al. | |
| 2008/0154192 A1 | 6/2008 | Schraga | |
| 2009/0275916 A1 | 11/2009 | Harms et al. | |
| 2011/0071482 A1 | 3/2011 | Selevan | |
| 2011/0257602 A1 * | 10/2011 | Watanabe | A61M 5/20 604/189 |
| 2012/0184909 A1 | 7/2012 | Gyrn | |
| 2013/0116665 A1 | 5/2013 | Humayun et al. | |
| 2013/0116666 A1 | 5/2013 | Shih et al. | |
| 2013/0204227 A1 | 8/2013 | Bochenko et al. | |
| 2015/0133859 A1 | 5/2015 | Caspers et al. | |

FOREIGN PATENT DOCUMENTS

| | | |
|---|---|---|
| EP | 0937471 A2 | 8/1999 |
| EP | 0937476 A2 | 8/1999 |
| EP | 2335755 A1 | 6/2011 |
| EP | 2357013 A1 | 8/2011 |
| WO | 1999/38554 A1 | 8/1999 |
| WO | 2001/10484 A1 | 2/2001 |
| WO | 2005/077441 A2 | 8/2005 |
| WO | 2010/073452 A1 | 7/2010 |
| WO | 2011/117404 A2 | 9/2011 |

OTHER PUBLICATIONS

Japanese Office Action for Application No. 2014-553765, dated Nov. 1, 2016, 4 pages, translation.

* cited by examiner

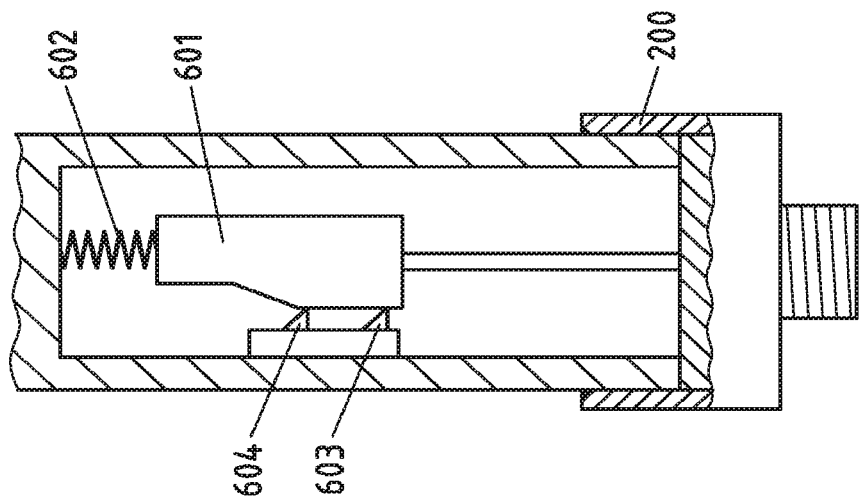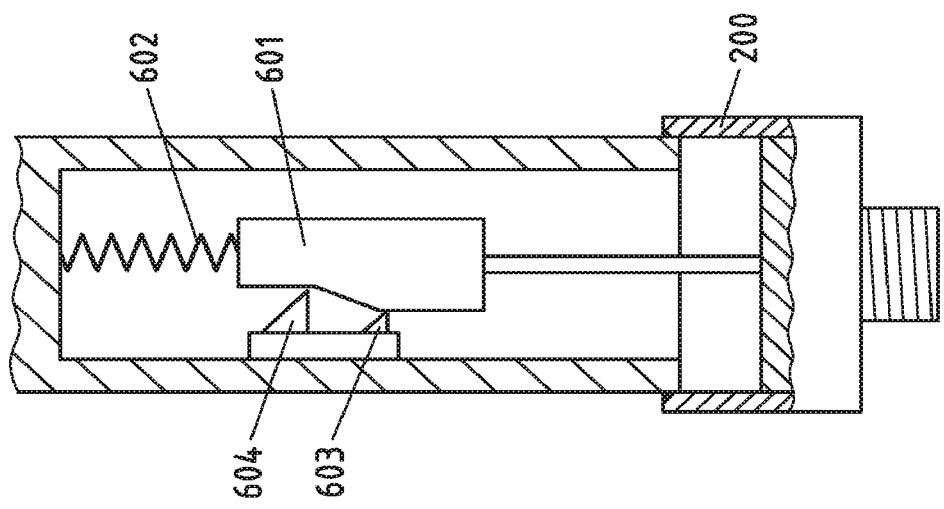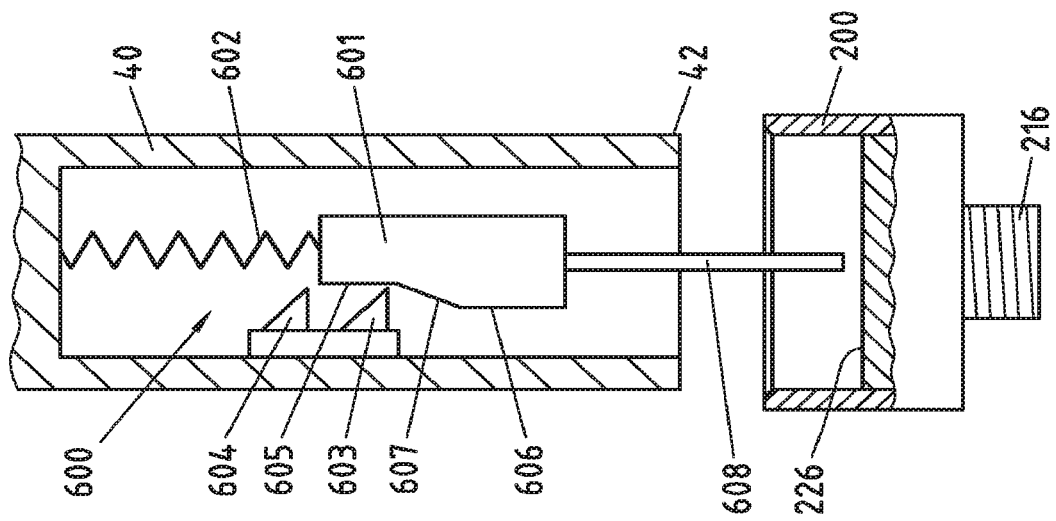

LIMITING LIFE TIME OF DISPENSE ASSEMBLY

This application is a continuation of U.S. patent application Ser. No. 14/373,088 filed Jul. 18, 2014, which is a U.S. National Stage entry of PCT Application Number PCT/EP2013/051901 filed Jan. 31, 2013, which claims priority to European Patent Application Number 12153382.2 filed Jan. 31, 2012, the contents of each of which is incorporated by reference in its entirety.

The present patent application relates to medical devices for delivering at least one drug agent, in particular two drug agents from separate reservoirs. Such drug agents may comprise a first and a second medicament. The medical device includes a dose setting mechanism for delivering the drug agents automatically or manually by the user.

The medical device can be an injector, for example a hand-held injector, especially a pen-type injector, that is an injector of the kind that provides for administration by injection of medicinal products from one or more multidose cartridges. In particular, the present invention relates to such injectors where a user may set the dose.

The drug agents may be contained in two or more multiple dose reservoirs, containers or packages, each containing independent (single drug compound) or pre-mixed (co-formulated multiple drug compounds) drug agents.

Certain disease states require treatment using one or more different medicaments. Some drug compounds need to be delivered in a specific relationship with each other in order to deliver the optimum therapeutic dose. The present patent application is of particular benefit where combination therapy is desirable, but not possible in a single formulation for reasons such as, but not limited to, stability, compromised therapeutic performance and toxicology.

For example, in some cases it may be beneficial to treat a diabetic with a long acting insulin (also may be referred to as the first or primary medicament) along with a glucagon-like peptide-1 such as GLP-1 or GLP-1 analog (also may be referred to as the second drug or secondary medicament).

Accordingly, there exists a need to provide devices for the delivery of two or more medicaments in a single injection or delivery step that is simple for the user to perform without complicated physical manipulations of the drug delivery device. The proposed drug delivery device provides separate storage containers or cartridge retainers for two or more active drug agents. These active drug agents are then combined and/or delivered to the patient during a single delivery procedure. These active agents may be administered together in a combined dose or alternatively, these active agents may be combined in a sequential manner, one after the other.

The drug delivery device also allows for the opportunity of varying the quantity of the medicaments. For example, one fluid quantity can be varied by changing the properties of the injection device (e.g., setting a user variable dose or changing the device's "fixed" dose). The second medicament quantity can be changed by manufacturing a variety of secondary drug containing packages with each variant containing a different volume and/or concentration of the second active agent.

The drug delivery device may have a single dispense interface. This interface may be configured for fluid communication with a primary reservoir and with a secondary reservoir of medicament containing at least one drug agent. The drug dispense interface can be a type of outlet that allows the two or more medicaments to exit the system and be delivered to the patient.

The combination of compounds from separate reservoirs can be delivered to the body via a double-ended needle assembly. This provides a combination drug injection system that, from a user's perspective, achieves drug delivery in a manner that closely matches the currently available injection devices that use standard needle assemblies. One possible delivery procedure may involve the following steps:

1. Attach a dispense interface to a distal end of the electro-mechanical injection device. The dispense interface comprises a first and a second proximal needle. The first and second needles pierce a first reservoir containing a primary compound and a second reservoir containing a secondary compound, respectively.

2. Attach a dose dispenser, such as a double-ended needle assembly, to a distal end of the dispense interface. In this manner, a proximal end of the needle assembly is in fluidic communication with both the primary compound and secondary compound.

3. Dial up/set a desired dose of the primary compound from the injection device, for example, via a graphical user interface (GUI).

4. After the user sets the dose of the primary compound, the micro-processor controlled control unit may determine or compute a dose of the secondary compound and preferably may determine or compute this second dose based on a previously stored therapeutic dose profile. It is this computed combination of medicaments that will then be injected by the user. The therapeutic dose profile may be user selectable. Alternatively, the user can dial or set a desired dose of the secondary compound.

5. Optionally, after the second dose has been set, the device may be placed in an armed condition. The optional armed condition may be achieved by pressing and/or holding an "OK" or an "Arm" button on a control panel. The armed condition may be provided for a predefined period of time during which the device can be used to dispense the combined dose.

6. Then, the user will insert or apply the distal end of the dose dispenser (e.g. a double ended needle assembly) into the desired injection site. The dose of the combination of the primary compound and the secondary compound (and potentially a third medicament) is administered by activating an injection user interface (e.g. an injection button).

Both medicaments may be delivered via one injection needle or dose dispenser and in one injection step. This offers a convenient benefit to the user in terms of reduced user steps compared to administering two separate injections.

As described above, since the dispense interface provides at least a part of the fluid channel for the fluids to be dispensed, the dispense interface is on the one hand in fluid communication with at least one reservoir of the medical device and thus one or more drug agents. On the other hand, over a needle assembly attached to or integrated in the dispense interface, the dispense interface is also in contact with the ambient air, the patients skin and/or the patients blood. However, it is problematic that the dispense interface is in direct contact with these latter non-sterile or contaminated fluids, gases and/or particles.

In general, a part of the fluid to be dispensed remains in the fluidic channels of the dispense interface. Over time the probability of the remaining fluid being contaminated increases. Moreover, after a certain time microbial growth can occur.

Additionally, the quality of the fluidic channels may deteriorate over time and/or certain substances present in the materials used for the fluidic channels of the dispense interface may migrate into the remaining fluid within the dispense interface.

The probability of too high levels of contamination of the remaining fluids in the dispense interface can be reduced by preservative agents present in the drug agents. However, these preservative agents can lose efficacy or can be absorbed over time by the material of the dispense interface.

It is, however, not desired to let a user of the medical device inject these remaining contaminated fluids into his or her body with a subsequent dispense step, since this constitutes risks and may be harmful for the user's health.

It is also possible, that the channels of the dispense interface are blocked, due to dried and/or clotted channels in the dispense interface. This can result in malfunctions of the medical device. In particular, this can make the user believe that a certain dose has been delivered even though there was no dose delivered. Hence, even life threatening situations can occur.

For these risks not to occur, the user would have to laboriously rinse the fluidic channels, wasting part of the medicaments or check somehow whether the medical device still ejects fluids. But even then, the user cannot be sure that both medicaments will be delivered or that the fluid dispensed will be sterile enough.

In view of the aforementioned, the invention faces the technical problem of providing a medical device which minimizes the risks described above. In particular it is an object of the present invention to provide a medical device, which exhibits an increased safety of the device and facilitates a safe use.

The technical problem is solved by a medical device for delivering at least one drug agent, comprising a sensor, a control unit and an attachable dispense assembly, wherein the sensor is configured to detect attachment of the dispense assembly to the medical device, wherein the control unit is configured to determine at least based on a signal from the sensor whether the end of life of the dispense assembly is reached and wherein the medical device is configured to indicate the end of life of the dispense assembly. The end of life of the dispense assembly may for example be determined by expiry of a timer that is started when the dispense assembly is attached.

By providing a medical device according to the invention, the beginning of the service life of the dispense assembly is detected by utilizing the point in time of attachment of the dispense assembly for determining the beginning of the service life of the dispense assembly. When the end of life or service life of the dispense assembly is reached, the medical device indicates the end of life of the dispense assembly and the user does not need to care about whether the dispense assembly may have deteriorated or is contaminated due to microbial growth or the like. As a result the medical device exhibits an increased safety of the device and facilitates a safe use.

When utilizing the point in time of attachment of the medical device to determine the end of life of the dispense assembly and indicating the end of life, the risk of dispensing a fluid with too high contamination can be reliably minimized.

A dispense assembly according to the invention is understood to be a separate element from the rest of the medical device being a main body or a cartridge holder, for example. The dispense assembly in particular exhibits one or more channels to be able to guide the fluids of the medical device to the users body. The dispense assembly can already exhibit an appropriate injection needle or cannula to pierce the user's skin. Though, it is also conceivable that the injection needle is designed as a separate element from the dispense assembly. In the latter case the dispense assembly is generally referred to as dispense interface with an attachable needle or cannula. A dispense assembly can in particular comprise a manifold and valves to further increase safety of the device and reduce the amount of undesired fluids in the channels.

The main body or the cartridge holder is then configured to receive the dispense assembly. The attachment of the dispense assembly to the main body can be realized in different ways. For instance, the dispense assembly can be attached via form fit or force fit, in particular the dispense assembly can be latched or screwed to the main body. A quick and reliable attachment can be realized in this way.

The control unit is preferably positioned in the main body or cartridge holder of the medical device and is configured to receive a signal from the sensor. Control unit is understood to be or comprise any kind of micro-processor or micro-controller, for example.

The sensor can be designed in various ways. It is possible to provide a mechanical switch, which is activated when the dispense assembly is attached. The sensor can also be designed as an electrical contact, such that a current or a voltage can be detected as soon as the dispense assembly is attached. It is further conceivable to design the sensor as a optical instrument. This may be a light barrier, a camera, a barcode reader, a proximity sensor or the like. In order to further increase safety and/or functionality, multiple identical or different sensors can be provided.

By determining the end of life of the dispense assembly based at least partially on the signal from the sensor it is meant that the signal of the sensor and hence for example the time of attachment of the dispense assembly influences the end of life of the dispense assembly. For instance, it is possible to start a timer when the dispense assembly is attached and to use the time as single criterion, whether the end of life of the dispense assembly is reached.

It is alternatively or additionally also possible to use different information for example, whether the temperature rose over a certain limit since the dispense assembly was attached or how often the dispense assembly was used since the dispense assembly was attached. For this, an additional temperature sensor or a counter is necessary, respectively. Combinations of these criterions are possible, as well.

The signal of the sensor can be an electrical pulse or a constant signal. A pulse can indicate the point in time of attachment and/or detachment of the dispense assembly, while a constant signal can constantly indicate, whether the dispense assembly is still attached.

The dispense assembly can be configured to determine the end of life of the dispense assembly in certain intervals and/or before each dispense.

Finally, by indicating the end of life of a dispense assembly, the user can be made aware, that the dispense assembly should not or cannot be used anymore. Such an indication can be provided by the medical device via a display or by means of a sound signal, for instance. It is also possible to implicitly indicate the end of life of the dispense assembly by preventing the use of the medical device.

According to a preferred embodiment of the medical device according to the invention, the control unit is configured to prevent further usage of the medical device when the end of life of the dispense assembly is reached. A particular safe usage of the medical device can be realized in this way, since the user cannot accidentally or on purpose use the medical device with the dispense assembly which end of life has already been reached.

The prevention of usage can be achieved by the software not allowing any executions of dispense actions, for example. It is also possible to mechanically lock the device in order to prevent any dispense of fluids from the medical device.

It is possible that only the dispense function of the device is disabled, preferably in combination with an indication on a display of the device. Hence, the device can still be used to access information saved on the device, such as the history of previous dispenses.

It is particularly preferred though that the user is guided through the exchange procedure of a dispense assembly, for example by displayed information such as "dispense interface expired" and/or "please remove dispense interface", and that during this exchange procedure the user cannot access any further information on the device.

The usage of the medical device is only prevented until a new dispense assembly is attached. To make sure that the same dispense assembly is not attached twice, it is conceivable to provide the dispense assembly with identification tags, which can be read by the medical device, for example with a barcode reader. A re-attachment of the same dispense assembly will then not lead to a reactivation of the dispense function.

It is further preferred that the control unit is configured to start a timer when the sensor indicates attachment of a dispense assembly. When the timer reaches or exceeds a certain time limit, the dispense assembly has reached its end of life. This is a particular easy possibility to determine the end of life of the dispense assembly. Such a period can be several days or weeks, for example. The time limit can be predetermined, for example. The timer can be implemented in the control unit, for instance.

That the total time of attachment is used to determine the end of life of the dispense assembly does not mean that other factors can be used to further improve the determination of the end of life. For example, as already mentioned above, further information, such as the number of dispenses or the temperature, can be used to modify the point in time, when the end of life has been reached.

In case there are different types of dispense assemblies, it is also conceivable to modify the time limit, after which the end of life has been reached, in dependence of the dispense assembly used. For this purpose an identification tag on the dispense assembly can provide information from which a time limit for the end of life can be deduced.

However, it can be economical and sufficient to exclusively use a fixed time limit to determine the end of life of the dispense assembly.

In case the timer is still running when a new dispense assembly is attached, the timer can be stopped and started again or simply reset.

According to a next embodiment of a medical device according to the invention, the sensor is configured to detect detachment of the dispense assembly from the medical device. This facilitates a safe use of the medical device, because the user can explicitly be instructed to attach a new dispense assembly, for example over a display of the medical device. The detachment can also be used to reset the timer of the medical device.

Depending on the kind of sensor used, the detachment of the dispense assembly can be realized by the sensor either by a second actuation of a switch or by disconnecting an electrical contact, for example.

It is preferred that the medical device further comprises at least a first reservoir containing a first fluid and a second reservoir containing a second fluid. The dispense assembly is in that case fluidly connected to both reservoirs. However, valves can be provided to reduce or eliminate mutual fluid connections between the reservoirs. At least one, preferably both of these fluids are drug agents and contain a medicament.

Particularly for medical devices containing more than one fluid, the device according to the invention can improve safety and facilitate safe use. The two fluids which normally need to be stored in different reservoirs are in contact with each other in the dispense assembly. The mixture remaining in the dispense assembly can further promote contamination, microbial growth or clotting of the dispense assembly.

It is advantageous, if the dispense assembly comprises a mechanical lock-out mechanism to prevent re-attachment of the dispense assembly to the medical device. This allows the dispense assembly to be attached only once by simple mechanical means. After the dispense assembly has been detached for the first time, the lock out mechanism is brought in a state that prevents any re-attachment. Expensive systems such as barcode readers and identification tags on the dispense assemblies to assure no second use of a dispense assembly are not necessary. The combination of indicating the end of life and preventing the re-attachment of the same dispense assembly by a mechanical lock-out mechanism has the effect of providing a particular safe medical device, which facilitates safe handling of the device.

The lock-out mechanism can generally be realized by certain locking elements provided by the dispense assembly, which locking elements are brought into an interference position when removing the dispense assembly from the medical device. The lock-out mechanism can be implemented by a lock-out spring integrated in the dispense assembly, for example. This spring is configured such that it first allows for attaching the dispense assembly. The attachment can then trigger or bend the lock-out spring in such a way, that spring arms of the lockout spring when detaching the dispense assembly move in a position preventing a second attachment.

The medical device according to the invention is particularly advantageous when the medical device is a portable drug delivery device. Portable devices are designed and intended to be used in a variety of situations and locations. This makes a portable drug delivery device particularly prone to contaminations of the fluids in the dispense assembly.

According to a second aspect of the invention the technical problem is further solved by a method comprising the steps of detecting an attachment of a dispense assembly to a medical device, in particular a medical device according to the invention, determining whether the end of life of the dispense assembly is reached and indicating the end of life of the dispense assembly.

By providing a method according to the invention, the beginning of the service life of the dispense assembly is detected by utilizing the point in time of attachment of the dispense assembly for determining the beginning of the service life of the dispense assembly. When the end of life or service life of the dispense assembly is reached, the method allows for indicating the end of life of the dispense assembly and the user does not need to care about whether the dispense assembly may have deteriorated or is contaminated due to microbial growth or the like. As a result the medical device exhibits an increased safety of the device and facilitates a safe use.

When utilizing the point in time of attachment of the medical device to determine the end of life of the dispense assembly and indicating the end of life, the risk of dispensing a fluid with too high contamination can be reliably minimized.

The detection of the attachment can be realized by a sensor, while the indication of the end of life of the dispense assembly is preferably realized by displaying such information on a screen of the medical device.

The determination whether the end of life of the dispense assembly has been reached can be performed constantly, regularly and/or before a dispense takes place, for instance.

It is preferred that the method according to the invention, further comprises the step of preventing further usage of the medical device when the end of life of the dispense assembly is reached.

The prevention of further usage can by realized by a control unit preventing any further dispense of the fluids, for example, as long as the dispense assembly is not exchanged.

It is further preferred that the method according to the invention further comprises the step of starting a timer when the dispense assembly is attached.

The end of life of the dispense assembly can thus be determined on how long the dispense assembly is attached to the medical device. The starting of the timer is initiated by the signal from the sensor, signaling an attachment of a dispense assembly. When a certain time limit, which may be fixed or adjustable, is reached or exceeded the end of life of the dispense assembly is indicated.

For further advantages and preferred embodiments of the method according to the invention it is referred to the description of the medical device according to the invention.

According to a third aspect of the present invention, further a program is disclosed comprising program code for performing the method according to the present invention and all exemplary embodiments thereof, when the program is executed on a processor.

The program may for instance be distributed via a network, such as for instance the Internet. The program may for instance be stored or encoded on a readable medium, for instance a computer-readable or processor-readable medium. The readable medium may for instance be embodied as an electric, magnetic, electro-magnetic, optic or other storage medium, and may either be a removable medium or a medium that is fixedly installed in an apparatus or device. The readable medium may for instance be a tangible medium, for instance a tangible storage medium.

BRIEF DESCRIPTION OF THE DRAWINGS

These as well as other advantages of various aspects of the present invention will become apparent to those of ordinary skill in the art by reading the following detailed description, with appropriate reference to the accompanying drawings, in which:

FIG. 12*a-c* illustrate a cross-sectional view of an exemplary embodiment of an attachable dispense interface and a sensor;

DETAILED DESCRIPTION

Figure 1:
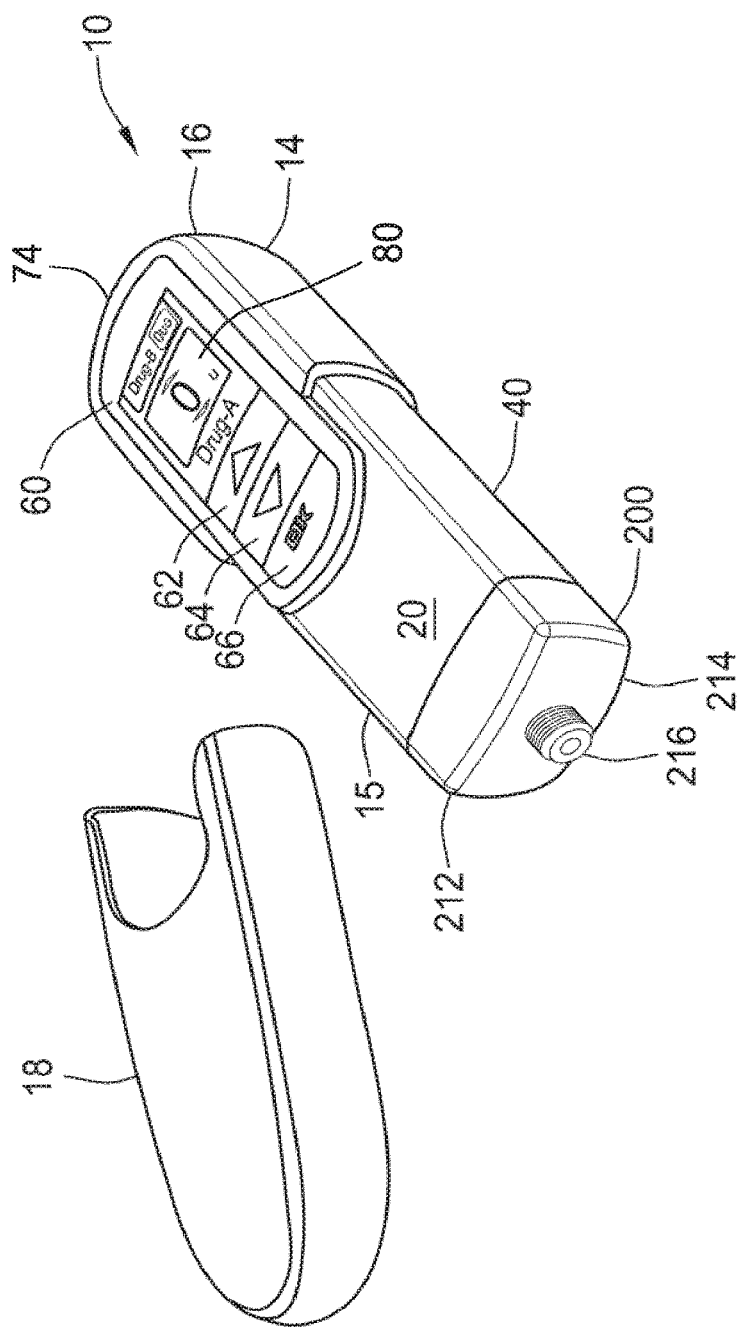
FIG. 1 illustrates a perspective view of an exemplary embodiment of a delivery device according to the invention with an end cap of the device removed.
Figure 2:
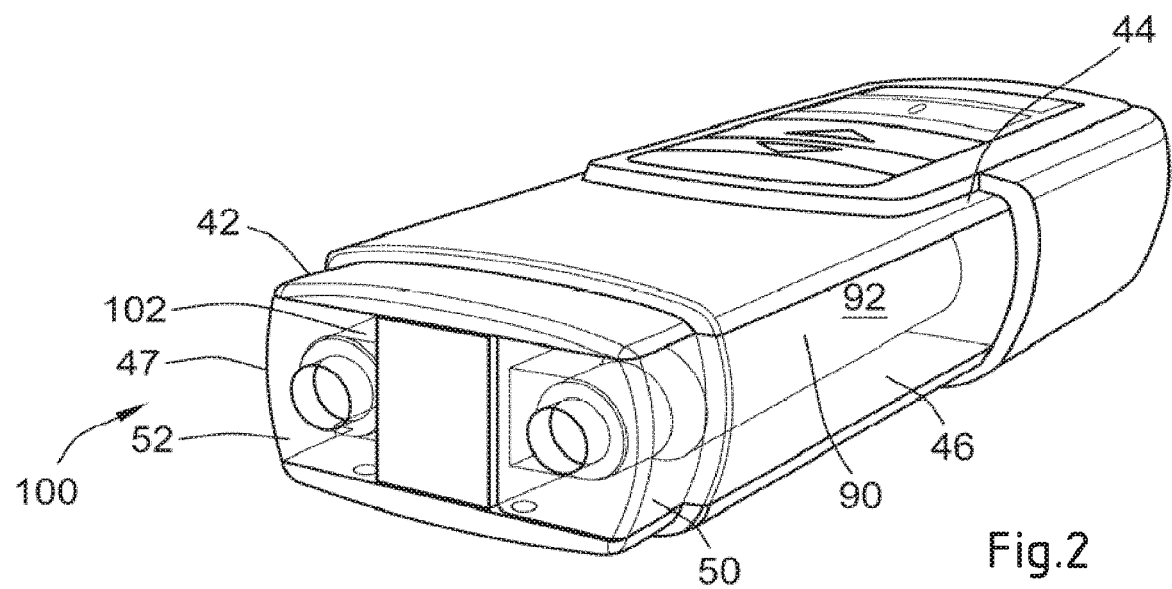
FIG. 2 illustrates a perspective view of the delivery device distal end showing the cartridge.

The drug delivery device as an exemplary embodiment of medical device according to the invention illustrated in FIG. 1 comprises a main body 14 that extends from a proximal end 16 to a distal end 15. At the distal end 15, a removable end cap or cover 18 is provided. This end cap 18 and the distal end 15 of the main body 14 work together to provide a snap fit or form fit connection so that once the cover 18 is slid onto the distal end 15 of the main body 14, this frictional fit between the cap and the main body outer surface 20 prevents the cover from inadvertently falling off the main body.

The main body 14 contains a micro-processor control unit, an electro-mechanical drive train, and at least two medicament reservoirs. When the end cap or cover 18 is removed from the device 10 (as illustrated in FIG. 1), a dispense interface 200 is mounted to the distal end 15 of the main body 14, and a dose dispenser (e.g., a needle assembly) is attached to the interface. The drug delivery device 10 can be used to administer a computed dose of a second medicament (secondary drug compound) and a variable dose of a first medicament (primary drug compound) through a single needle assembly, such as a double ended needle assembly.

The drive train may exert a pressure on the bung of each cartridge, respectively, in order to expel the doses of the first and second medicaments. For example, a piston rod may push the bung of a cartridge forward a pre-determined amount for a single dose of medicament. When the cartridge is empty, the piston rod is retracted completely inside the main body 14, so that the empty cartridge can be removed and a new cartridge can be inserted.

A control panel region 60 is provided near the proximal end of the main body 14. Preferably, this control panel region 60 comprises a digital display 80 along with a plurality of human interface elements that can be manipulated by a user to set and inject a combined dose. In this arrangement, the control panel region comprises a first dose setting button 62, a second dose setting button 64 and a third button 66 designated with the symbol "OK." Further buttons, such as a "back" button can be provided, as well. In addition, along the most proximal end of the main body, an injection button 74 is also provided (not visible in the perspective view of FIG. 1).

The cartridge holder 40 can in this case be removably attached to the main body 14 and may contain at least two cartridge retainers 50 and 52. Each retainer is configured so as to contain one medicament reservoir, such as a glass cartridge. Preferably, each cartridge contains a different medicament.

In addition, at the distal end of the cartridge holder 40, the drug delivery device illustrated in FIG. 1 includes a dispense interface 200 as an exemplary embodiment of a dispense assembly. The dispense interface 200 is attachable to the cartridge holder 40. As will be described in relation to FIG. 4, in one arrangement, this dispense interface 200 includes a main outer body 210 that is removably attached to a distal end 42 of the cartridge holder 40. As can be seen in FIG. 1, a distal end 214 of the dispense interface 200 preferably comprises a mounting hub 216. This mounting hub 216 may be configured so as to allow a dose dispenser, such as a conventional pen type injection needle assembly, to be removably mounted to the drug delivery device 10. The dispense interface 200 and the dose dispenser can also be designed as one piece.

Once the device is turned on, the digital display 80 shown in FIG. 1 illuminates and provides the user certain device information, preferably information relating to the medicaments contained within the cartridge holder 40. For example, the user is provided with certain information relating to both the primary medicament (Drug A) and the secondary medicament (Drug B).

Figure 3:
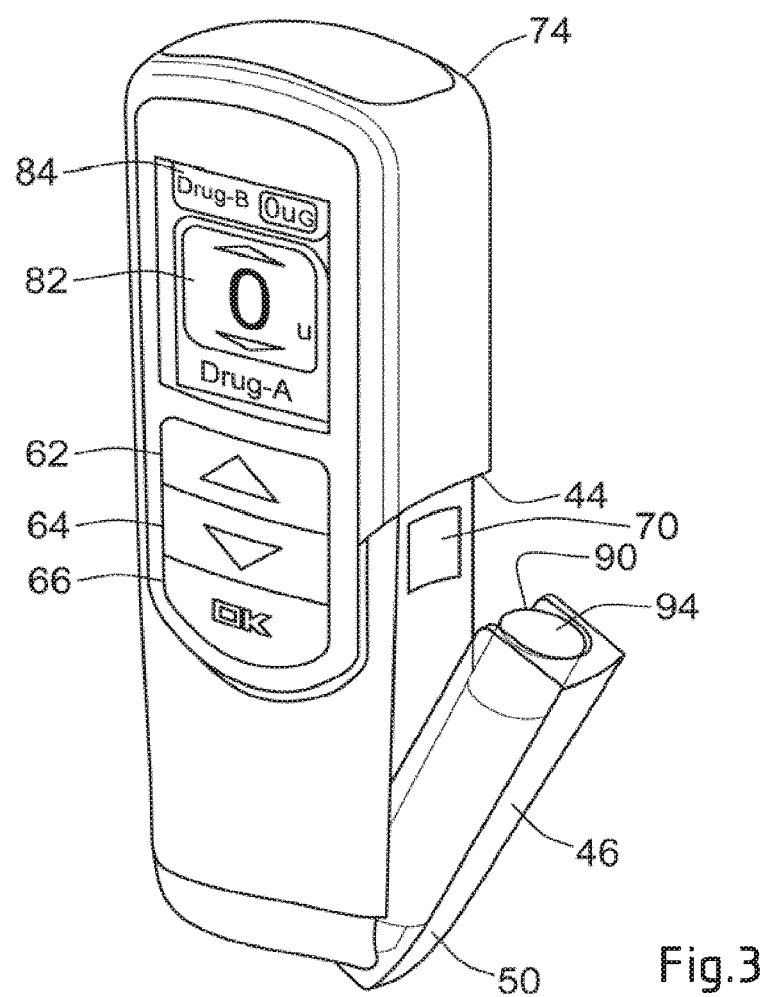
FIG. 3 illustrates a perspective view of the delivery device illustrated in FIG. 1 with one cartridge retainer in an open position.

As shown in FIG. 3, the first and second cartridge retainers 50, 52 may be hinged cartridge retainers. These hinged retainers allow user access to the cartridges. FIG. 3 illustrates a perspective view of the cartridge holder 40 illustrated in FIG. 1 with the first hinged cartridge retainer 50 in an open position. FIG. 3 illustrates how a user might access the first cartridge 90 by opening up the first retainer 50 and thereby having access to the first cartridge 90.

Figure 4:
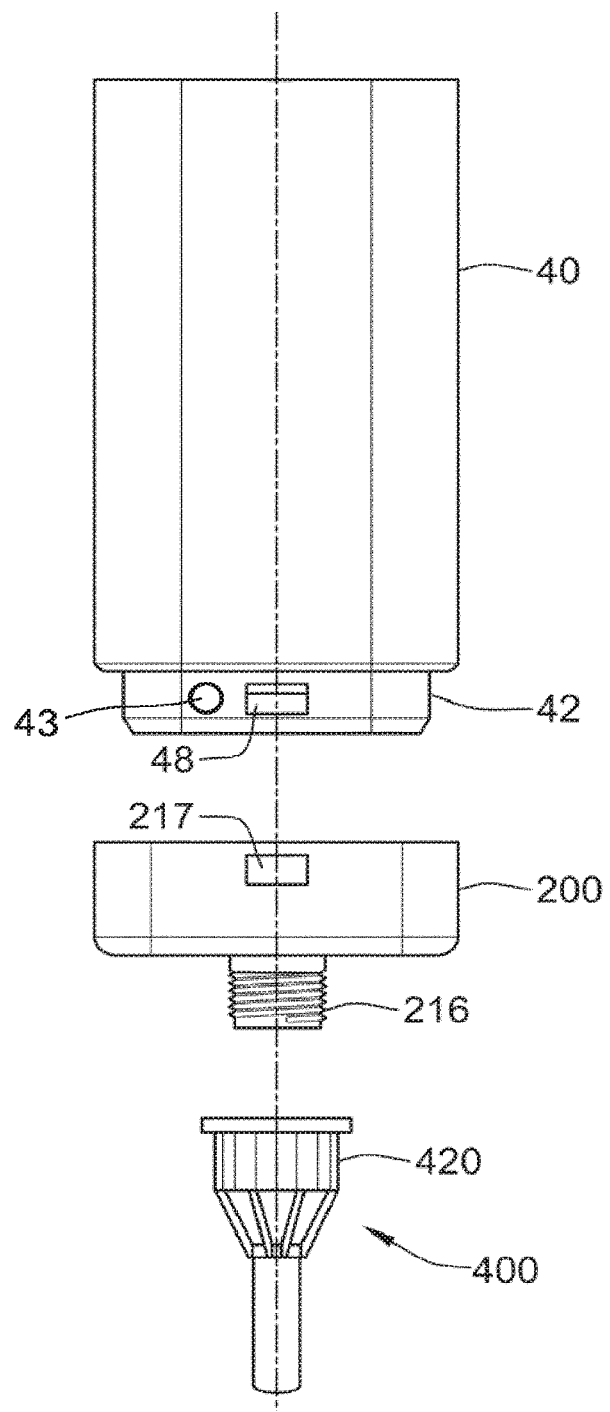
FIG. 4 illustrates an exemplary embodiment of a dispense interface and an exemplary embodiment of a dose dispenser that can be removably mounted on a distal end of the delivery device illustrated in FIG. 1.

As mentioned above when discussing FIG. 1, a dispense interface 200 is coupled to the distal end of the cartridge holder 40. FIG. 4 illustrates a flat view of the dispense interface 200 unconnected to the distal end of the cartridge holder 40. A dose dispenser or needle assembly that may be used with the interface 200 is also illustrated and is provided in a protective outer cap 420.

FIG. 4 also shows a sensor 43 at the distal end 42 of the cartridge holder 40. The sensor may be a light barrier, a camera, a barcode reader or a proximity sensor, for example. The sensor 43 is preferably of such design that it can substantially only be actuated by the dispense interface 200 being attached to the cartridge holder 40. The sensor 43 may be a switch situated in a recess for this purpose, which cannot accidentally be pressed or activated by the user directly, but activated by a latch on the dispense interface 200, which is adapted to the recess of the switch.

Figure 5:
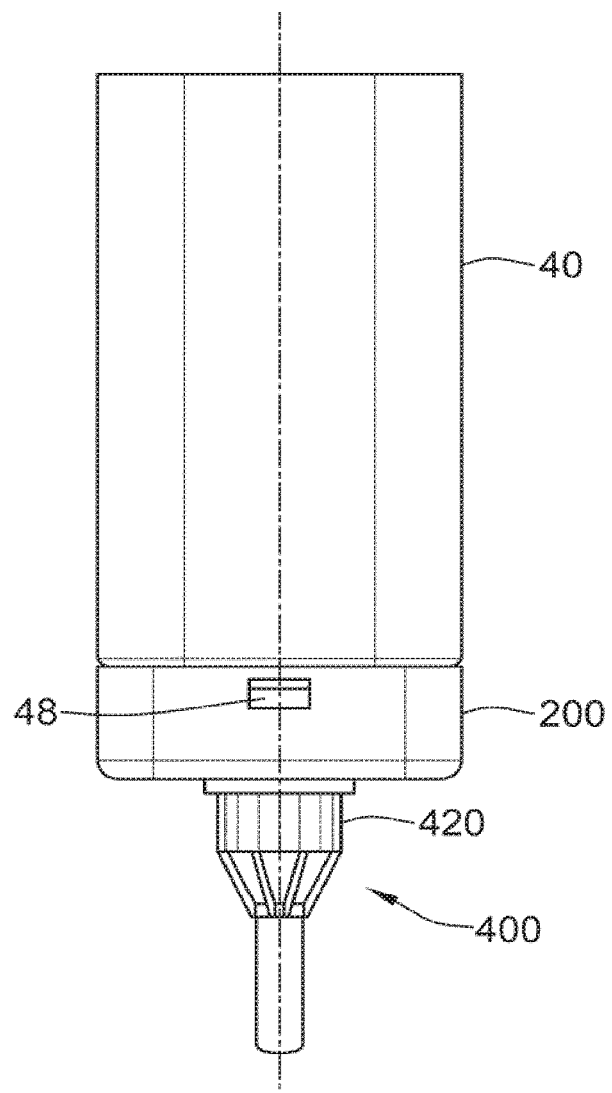
FIG. 5 illustrates the dispense interface and the dose dispenser illustrated in FIG. 4 mounted on a distal end of the delivery device illustrated in FIG. 1.

In FIG. 5, the dispense interface 200 illustrated in FIG. 4 is shown coupled to the cartridge holder 40. The axial attachment means between the dispense interface 200 and the cartridge holder 40 can be any known axial attachment means to those skilled in the art, including snap locks, snap fits, snap rings, keyed slots, and combinations of such connections. The connection or attachment between the dispense interface and the cartridge holder may also contain additional features (not shown), such as connectors, stops, splines, ribs, grooves, pips, clips and the like design features, that ensure that specific hubs are attachable only to matching drug delivery devices. Such additional features would prevent the insertion of a non-appropriate secondary cartridge to a non-matching injection device.

Figure 13:
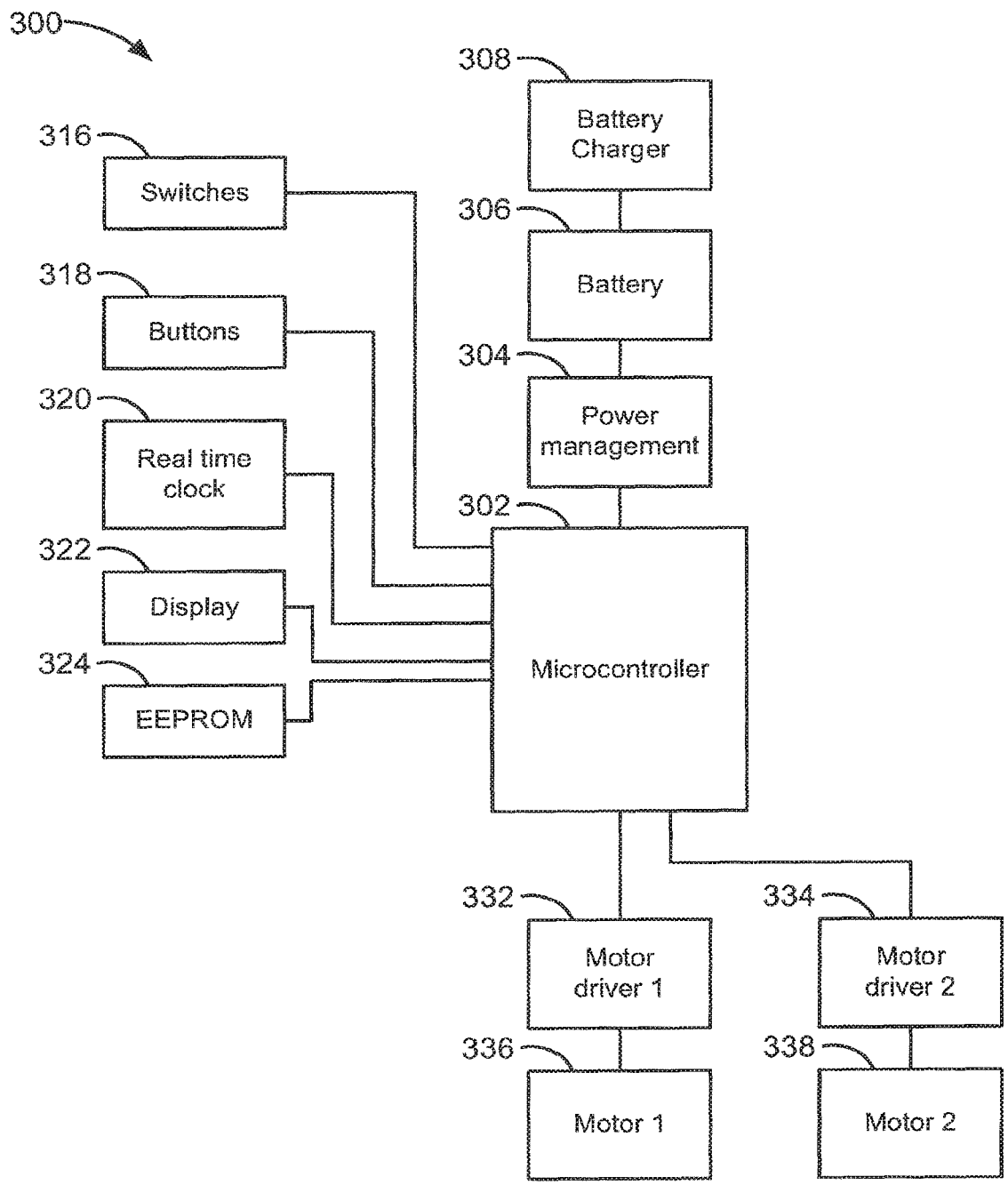
FIG. 13 illustrates a block diagram functional description of a control unit for operation off the drug delivery device illustrated in FIG. 1.
Figure 14:
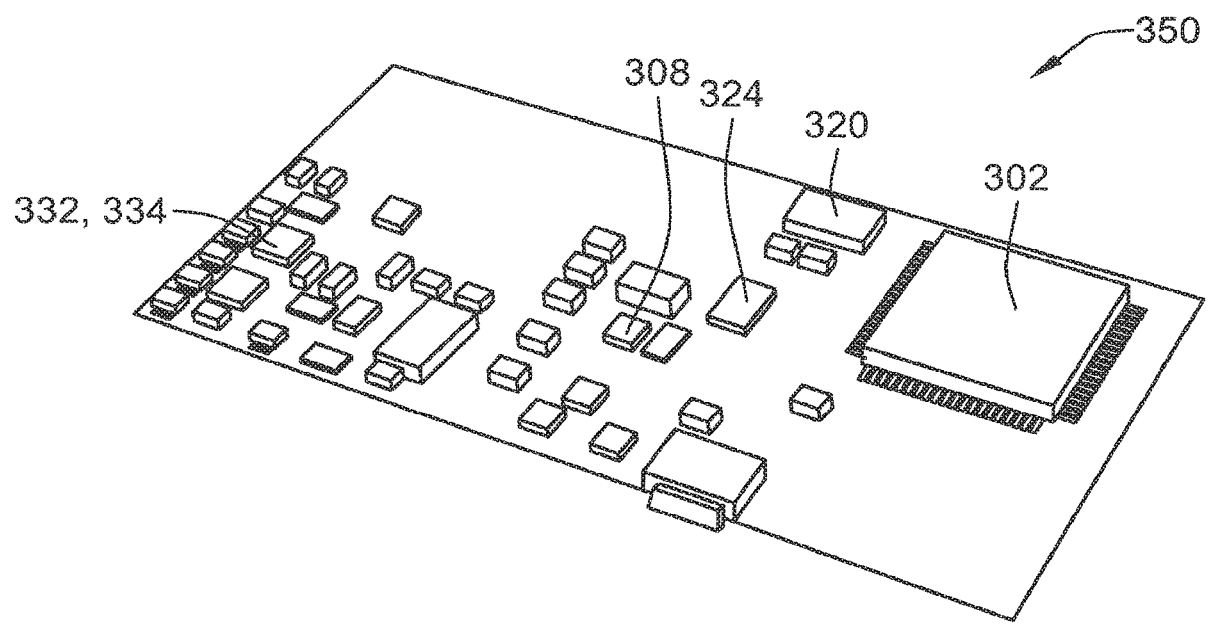
FIG. 14 illustrates a printed circuit board assembly of the drug delivery device illustrated in FIG. 1.

Since the dispense interface 200 is now properly attached to the cartridge holder 40 of the device 10, the sensor 43 will send a signal to a control unit, for example the micro-controller 302 (see FIGS. 13 and 14). The micro-controller 302 may start a timer, for example, in order to be able to determine the end of life of the dispense interface 200 in the future. In case a predetermined time limit is reached, the medical device will indicate the end of life of the dispense interface, for example on the display 80. The user can be requested to remove the dispense interface 200. To prevent any further use after the end of life of the dispense interface has been reached, the micro-controller 302 can prevent any further dose delivery.

When the sensor 43 detects that the dispense interface 200 was removed, the user can be requested to attach an unused dispense interface 200. In case the sensor is a barcode reader and the dispense interfaces are provided with barcodes containing identity information, it is possible to prevent reuse of the same dispense interface, by reading the barcode and checking whether a new dispense interface has been attached before allowing further use of the device.

Figure 6:
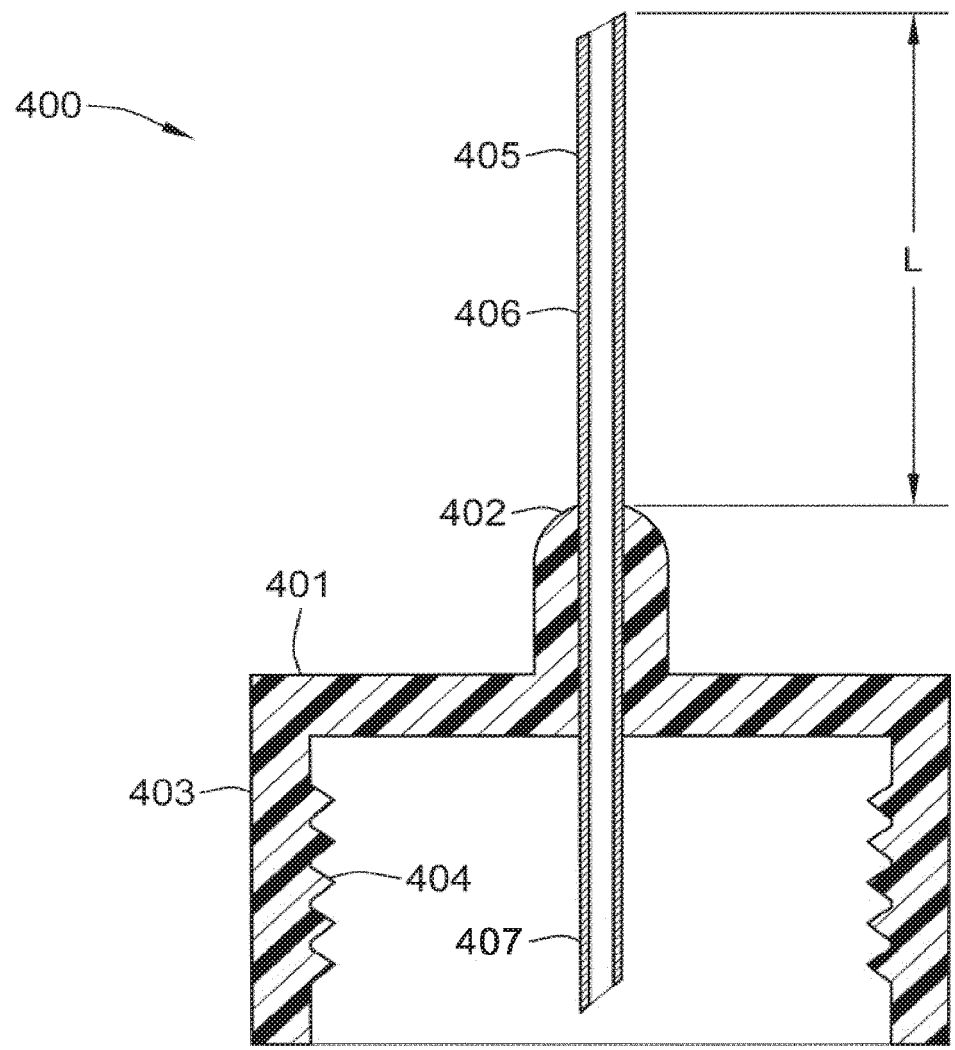
FIG. 6 illustrates one arrangement of a needle assembly that may be mounted on a distal end of the delivery device.
Figure 7:
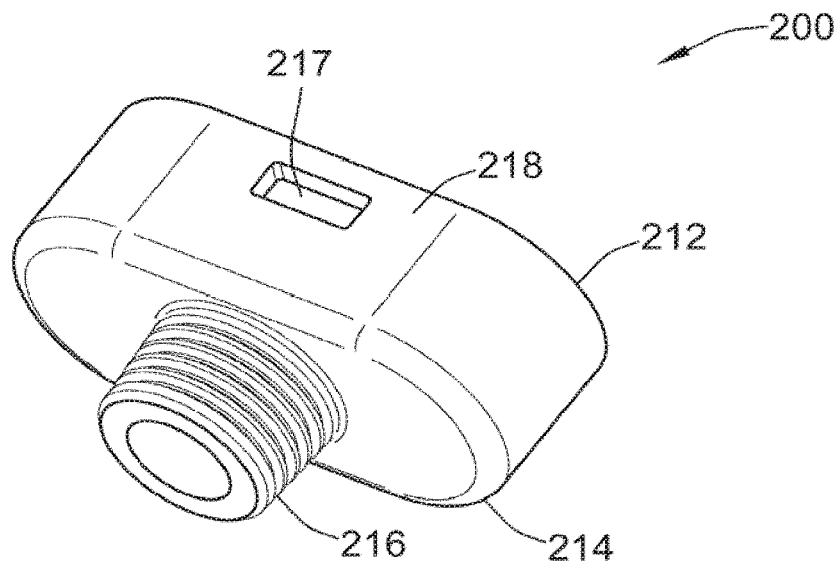
FIG. 7 illustrates a perspective view of the dispense interface illustrated in FIG. 4.

FIG. 5 also illustrates the double ended needle assembly 400 and protective cover 420 coupled to the distal end of the dispense interface 200 that may be screwed onto the needle hub of the interface 200. FIG. 6 illustrates a cross sectional view of the double ended needle assembly 400 mounted on the dispense interface 200 in FIG. 5.

The double ended needle assembly 400 illustrated in FIG. 6 comprises a double ended needle 406 and a needle hub 401. The double ended needle or cannula 406 is fixedly mounted in the needle hub 401. This needle hub 401 comprises a circular disk shaped element which has along its periphery a circumferential depending sleeve 403. Along an inner wall of this needle hub 401, a thread 404 is provided. This thread 404 allows the needle hub 401 to be screwed onto the dispense interface 200 which, in one preferred arrangement, is provided with a corresponding outer thread along a distal hub. At a center portion of the needle hub 401 there is provided a protrusion 402. This protrusion 402 projects from the hub in an opposite direction of the sleeve member. A double ended needle 406 is mounted centrally through the protrusion 402 and the needle hub 401. This double ended needle 406 is mounted such that a first or distal piercing end 405 of the double ended needle forms an injecting part for piercing an injection site (e.g., the skin of a user).

Similarly, a second or proximal piercing end 407 of the double ended needle assembly 400 protrudes from an opposite side of the circular disc so that it is concentrically surrounded by the sleeve 403. In one needle assembly arrangement, the second or proximal piercing end 407 may be shorter than the sleeve 403 so that this sleeve to some extent protects the pointed end of the back sleeve. The needle cover cap 420 illustrated in FIGS. 4 and 5 provides a form fit around the outer surface 403 of the needle hub 401.

Referring now to FIGS. 8 to 11, one preferred arrangement of this interface 200 will now be discussed. In this one preferred arrangement, this interface 200 comprises:
a. a main outer body 210,
b. an first inner body 220,
c. a second inner body 230,
d. a first piercing needle 240,
e. a second piercing needle 250,
f. a valve seal 260, and
g. a septum 270.

The main outer body 210 comprises a main body proximal end 212 and a main body distal end 214. At the proximal end 212 of the outer body 210, a connecting member is configured so as to allow the dispense interface 200 to be attached to the distal end of the cartridge holder 40. Preferably, the connecting member is configured so as to allow the dispense interface 200 to be removably connected the cartridge holder 40. In one preferred interface arrangement, the proximal end of the interface 200 is configured with an upwardly extending wall 218 having at least one recess. For example, as may be seen from FIG. 8, the upwardly extending wall 218 comprises at least a first recess 217 and a second recess 219.

Preferably, the first and the second recesses 217, 219 are positioned within this main outer body wall so as to cooperate with an outwardly protruding member located near the distal end of the cartridge holder 40 of the drug delivery device 10. For example, this outwardly protruding member 48 of the cartridge holder may be seen in FIGS. 4 and 5. A second similar protruding member is provided on the opposite side of the cartridge holder. As such, when the interface 200 is axially slid over the distal end of the cartridge holder 40, the outwardly protruding members will cooperate with the first and second recess 217, 219 to form an interference fit, form fit, or snap lock. Alternatively, and as those of skill in the art will recognize, any other similar connection mechanism that allows for the dispense interface and the cartridge holder 40 to be axially coupled could be used as well.

The main outer body 210 and the distal end of the cartridge holder 40 act to form an axially engaging snap lock or snap fit arrangement that could be axially slid onto the distal end of the cartridge holder. In one alternative arrangement, the dispense interface 200 may be provided with a coding feature so as to prevent inadvertent dispense interface cross use. That is, the inner body of the hub could be geometrically configured so as to prevent an inadvertent cross use of one or more dispense interfaces.

Figure 8:
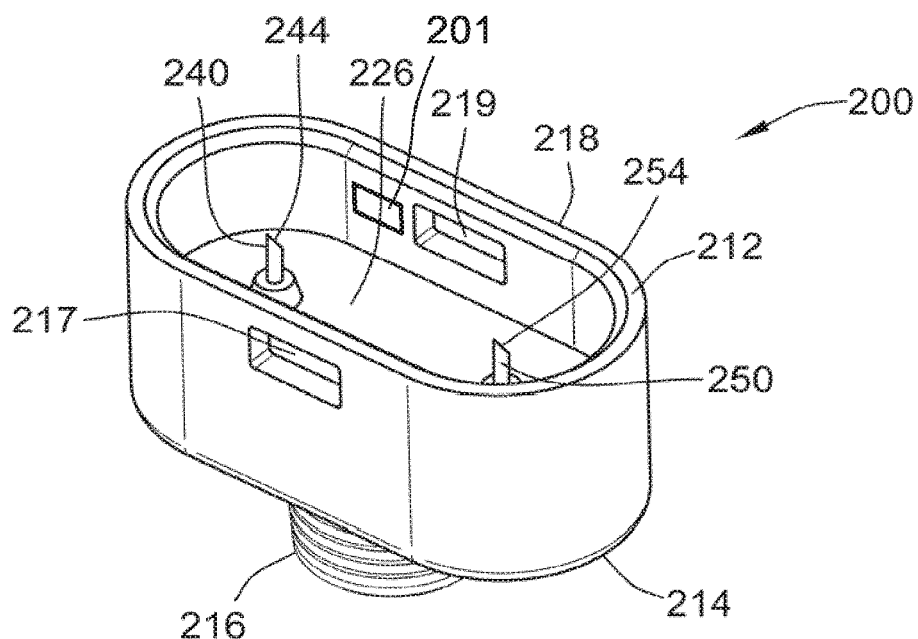
FIG. 8 illustrates another perspective view of the dispense interface illustrated in FIG. 4.
Figure 9:
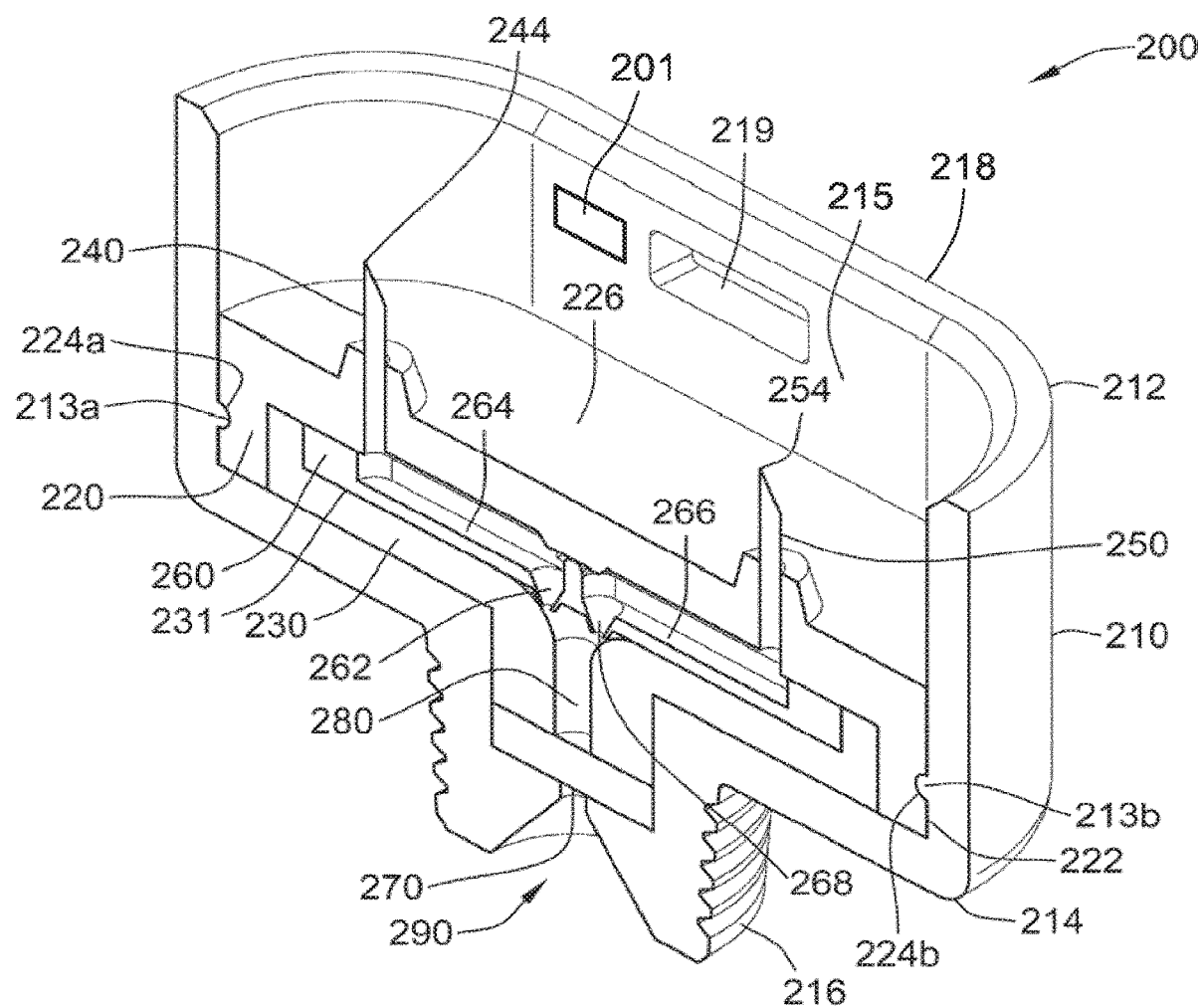
FIG. 9 illustrates a cross-sectional view of another embodiment of a dispense interface similar to the one illustrated in FIG. 4.
Figure 10:
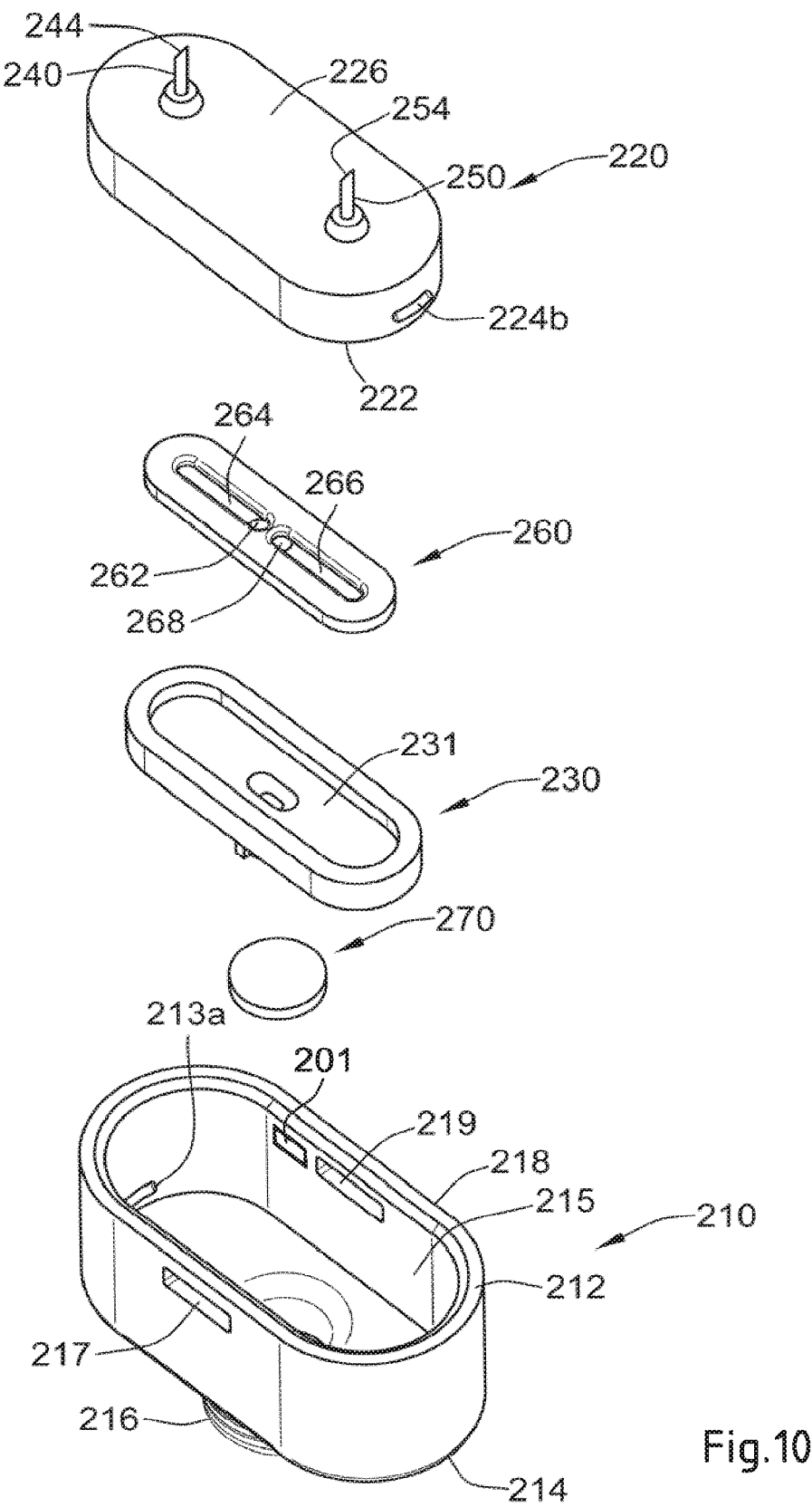
FIG. 10 illustrates an exploded view of the dispense interface illustrated in FIG. 4.

As can be further seen from the FIGS. 8, 9 and 10, the dispense interface 200 comprises an area 201, which can correlate with a sensor 43 as illustrated in FIG. 4. Such an specifically adapted area 201 can comprise a barcode for example, which is read by the sensor 43 in order to detect attachment of a dispense interface 200 or to detect whether the dispense interface 200 has already been used. Such an area 201 can also be a conductive area, for instance. The sensor 43 can in this case be two electrical contacts which detect the attachment of the dispense interface 200 when a current or voltage between the two contacts of the sensor 43 can be detected, which will be possible when the conductive area touches both electrical contacts of the sensor 43. When the dispense interface is removed and the contacts of the sensor 43 is interrupted the detachment of the dispense interface 200 can be detected.

A mounting hub 216 is provided at a distal end of the main outer body 210 of the dispense interface 200. Such a mounting hub 216 can be configured to be releasably connected to a needle assembly. As just one example, this mounting hub 216 may comprise an outer thread that engages an inner thread provided along an inner wall surface of a needle hub of a needle assembly, such as the needle hub 401 and the double ended needle assembly 400 illustrated in FIG. 6. Alternative mounting hubs 216 may also be provided such as a snap lock, a snap lock released through threads, a bayonet lock, a form fit, or other similar connection arrangements.

The dispense interface 200 further comprises a first inner body 220. Certain details of this inner body are illustrated in FIG. 8-11. Preferably, this first inner body 220 is coupled to an inner surface 215 of the extending wall 218 of the main outer body 210. More preferably, this first inner body 220 is coupled by way of a rib and groove form fit arrangement to an inner surface of the outer body 210. For example, as can be seen from FIG. 9, the extending wall 218 of the main outer body 210 is provided with a first rib 213a and a second rib 213b. This first rib 213a is also illustrated in FIG. 10. These ribs 213a and 213b are positioned along the inner surface 215 of the wall 218 of the outer body 210 and create a form fit or snap lock engagement with cooperating grooves 224a and 224b of the first inner body 220. In a preferred arrangement, these cooperating grooves 224a and 224b are provided along an outer surface 222 of the first inner body 220.

In addition, as can be seen in FIG. 8-10, a proximal surface 226 near the proximal end of the first inner body 220 may be configured with at least a first proximally positioned piercing needle 240 comprising a proximal piercing end portion 244. Similarly, the first inner body 220 is configured with a second proximally positioned piercing needle 250 comprising a proximally piercing end portion 254. Both the first and second needles 240, 250 are rigidly mounted on the proximal surface 226 of the first inner body 220.

Preferably, this dispense interface 200 further comprises a valve arrangement. Such a valve arrangement could be constructed so as to prevent cross contamination of the first and second medicaments contained in the first and second reservoirs, respectively. A preferred valve arrangement may also be configured so as to prevent back flow and cross contamination of the first and second medicaments.

In one preferred system, dispense interface 200 includes a valve arrangement in the form of a valve seal 260. Such a valve seal 260 may be provided within a cavity 231 defined by the second inner body 230, so as to form a holding chamber 280. Preferably, cavity 231 resides along an upper surface of the second inner body 230. This valve seal comprises an upper surface that defines both a first fluid groove 264 and second fluid groove 266. For example, FIG. 9 illustrates the position of the valve seal 260, seated between the first inner body 220 and the second inner body 230. During an injection step, this seal valve 260 helps to prevent the primary medicament in the first pathway from migrating to the secondary medicament in the second pathway, while also preventing the secondary medicament in the second pathway from migrating to the primary medicament in the first pathway. Preferably, this seal valve 260 comprises a first non-return valve 262 and a second non-return valve 268. As such, the first non-return valve 262 prevents fluid transferring along the first fluid pathway 264, for example a groove in the seal valve 260, from returning back into this pathway 264. Similarly, the second non-return valve 268 prevents fluid transferring along the second fluid pathway 266 from returning back into this pathway 266.

Together, the first and second grooves 264, 266 converge towards the non-return valves 262 and 268 respectively, to then provide for an output fluid path or a holding chamber 280. This holding chamber 280 is defined by an inner chamber defined by a distal end of the second inner body both the first and the second non return valves 262, 268 along with a pierceable septum 270. As illustrated, this pierceable septum 270 is positioned between a distal end portion of the second inner body 230 and an inner surface defined by the needle hub of the main outer body 210.

The holding chamber 280 terminates at an outlet port of the interface 200. This outlet port 290 is preferably centrally located in the needle hub of the interface 200 and assists in maintaining the pierceable seal 270 in a stationary position. As such, when a double ended needle assembly is attached to the needle hub of the interface (such as the double ended needle illustrated in FIG. 6), the output fluid path allows both medicaments to be in fluid communication with the attached needle assembly.

The hub interface 200 further comprises a second inner body 230. As can be seen from FIG. 9, this second inner body 230 has an upper surface that defines a recess, and the valve seal 260 is positioned within this recess. Therefore, when the interface 200 is assembled as shown in FIG. 9, the second inner body 230 will be positioned between a distal end of the outer body 210 and the first inner body 220. Together, second inner body 230 and the main outer body hold the septum 270 in place. The distal end of the inner body 230 may also form a cavity or holding chamber that can be configured to be fluid communication with both the first groove 264 and the second groove 266 of the valve seal.

Axially sliding the main outer body 210 over the distal end of the drug delivery device attaches the dispense interface 200 to the multi-use device. In this manner, a fluid communication may be created between the first needle 240 and the second needle 250 with the primary medicament of the first cartridge and the secondary medicament of the second cartridge, respectively.

Figure 11:
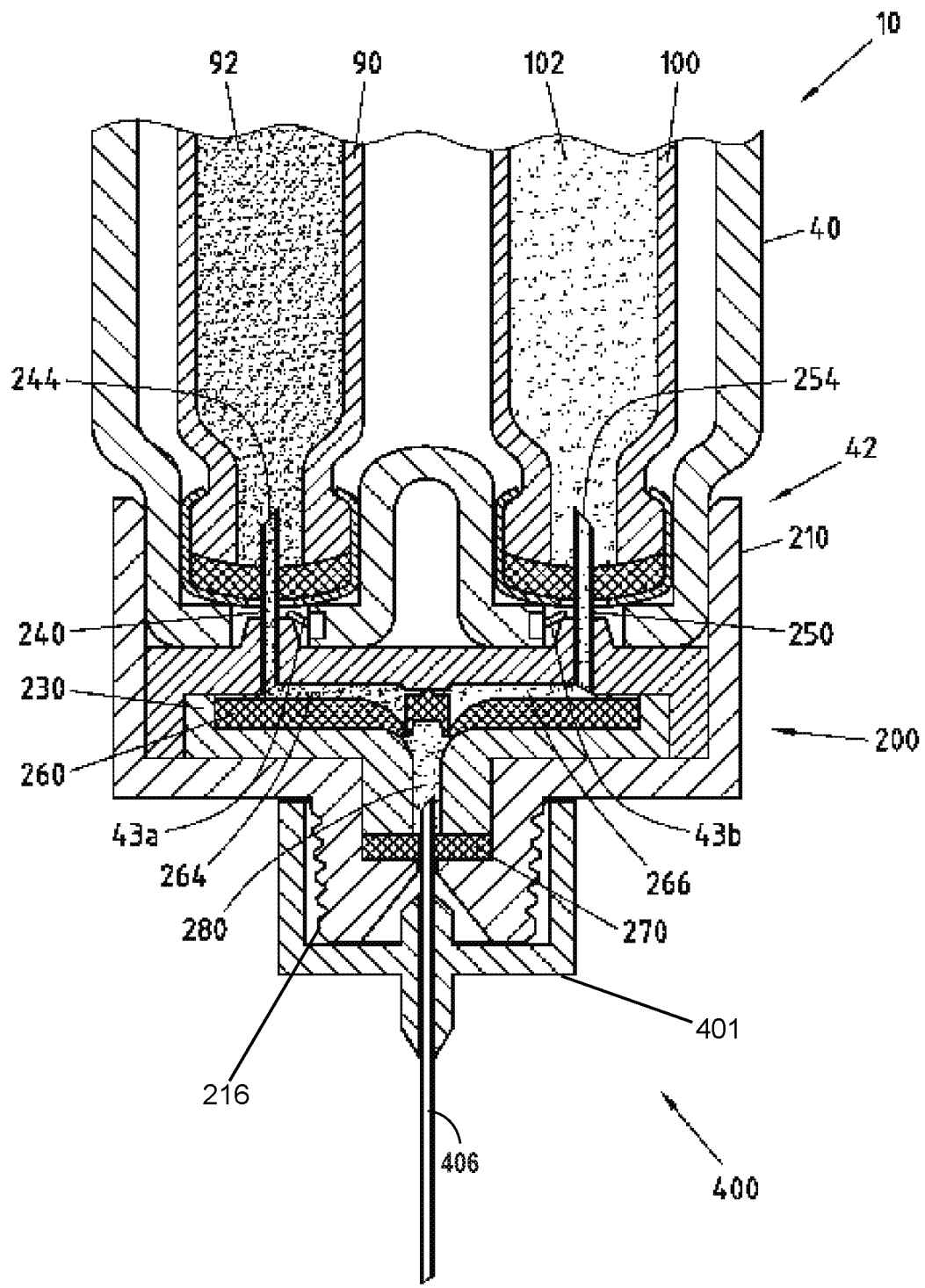
FIG. 11 illustrates a cross-sectional view of another exemplary embodiment of a dispense interface and needle assembly mounted onto a drug delivery device, similar to the device illustrated in FIG. 1.

FIG. 11 illustrates the dispense interface 200 after it has been mounted onto the distal end 42 of the cartridge holder 40 of the drug delivery device 10 illustrated in FIG. 1. A double ended needle 406 is also mounted to the distal end of this interface. The cartridge holder 40 is illustrated as having a first cartridge containing a first medicament and a second cartridge containing a second medicament.

When the interface 200 is first mounted over the distal end of the cartridge holder 40, the proximal piercing end 244 of the first piercing needle 240 pierces the septum of the first cartridge 90 and thereby resides in fluid communication with the primary medicament 92 of the first cartridge 90. A distal end of the first piercing needle 240 will also be in fluid communication with a first fluid path groove 264 defined by the valve seal 260.

Similarly, the proximal piercing end 254 of the second piercing needle 250 pierces the septum of the second cartridge 100 and thereby resides in fluid communication with the secondary medicament 102 of the second cartridge 100. A distal end of this second piercing needle 250 will also be in fluid communication with a second fluid path groove 266 defined by the valve seal 260.

FIG. 11 illustrates a preferred arrangement of such a dispense interface 200 that is coupled to a distal end 15 of the main body 14 of drug delivery device 10. Preferably, such a dispense interface 200 is removably coupled to the cartridge holder 40 of the drug delivery device 10.

As illustrated in FIG. 11, the dispense interface 200 is coupled to the distal end of a cartridge holder 40. This cartridge holder 40 is illustrated as containing the first cartridge 90 containing the primary medicament 92 and the second cartridge 100 containing the secondary medicament 102. Once coupled to the cartridge holder 40, the dispense interface 200 essentially provides a mechanism for providing a fluid communication path from the first and second cartridges 90, 100 to the common holding chamber 280. This holding chamber 280 is illustrated as being in fluid communication with a dose dispenser. Here, as illustrated, this dose dispenser comprises the double ended needle assembly 400. As illustrated, the proximal end of the double ended needle assembly is in fluid communication with the chamber 280.

In one preferred arrangement, the dispense interface is configured so that it attaches to the main body in only one orientation, that is it is fitted only one way round. As such as illustrated in FIG. 11, once the dispense interface 200 is attached to the cartridge holder 40, the primary needle 240 can only be used for fluid communication with the primary medicament 92 of the first cartridge 90 and the interface 200 would be prevented from being reattached to the holder 40 so that the primary needle 240 could now be used for fluid communication with the secondary medicament 102 of the second cartridge 100. Such a one way around connecting mechanism may help to reduce potential cross contamination between the two medicaments 92 and 102.

As can be further seen from FIG. 11, the cartridge holder 40 of medical device 10 further comprises two switches 43a and 43b as sensors at its distal end 42. The switches 43a, 43b will be activated, in this case pushed towards the reservoirs 90 and 100 respectively, when the dispense interface 200 is attached to the cartridge holder 40. The switches 43a, 43b indicate correct attachment of the dispense interface 200, when both switches 43a, 43b are activated and the attachment can be detected and a signal can be send to the control unit, for example the micro-controller 302. When the dispense interface is removed again, the switches may jump back into a state further away from the cartridges by the force of a spring (not shown), for example. In this way, the switches 43a, 43b can readily detect the next attachment of a dispense interface 200.

FIG. 12a to c illustrate a further embodiment of a sensor or a mechanism in order to detect a complete attachment of an attachable dispense assembly and a cross-sectional view of the attaching of the dispense interface 200 onto the drug delivery device 10 is illustrated. The drug delivery device 10 comprises a sensor in form of a detecting arrangement 600 comprising a push rod 601. For instance, the detecting arrangement 600 is at least partially arranged in a cavity formed by the cartridge holder 40.

At the proximal end of the push rod 601, a spring 602 is arranged which is connected to the cartridge holder 40 such that the push rod 601 is resiliently hold in the drug delivery device 10 and is at least longitudinally movable in the drug delivery device.

The detecting arrangement 600 further comprises a first switch 603 and a second switch 604 which are longitudinally arranged at a side-wall of the cavity 43. Therein, the first switch 603 is arranged closer to the distal end 42 of the cartridge holder 40 than the second switch. In other words, the first switch 603 is distally positioned and the second switch 604 is proximally positioned in the drug delivery device 10. The first switch 603 and the second switch 604 are pressure activated switches forming a first and a second detecting unit. In particular, the first switch 603 and the second switch 604 are only activated, when pressure is applied on the respective switch, and otherwise deactivated. The switches may be connected to a micro-processor control unit, such as the microcontroller 302 in FIG. 13, of the drug delivery device 10, logically signalling activation and deactivation to the micro-processor control unit.

A lateral surface of the push rod 601 oriented towards the first switch 603 and the second switch 604 is formed from three portions, two parallel surface portions 605, 606 and an inclined surface portion 607. The inclined surface portion 607 is arranged between the parallel surface portions 605, 606 such that the parallel surface portion 605 at the proximal end of the push rod is set back. A rod 608 is arranged at the distal end of the push rod 601.

In FIG. 12a, the dispense interface 200 is not attached to the drug delivery device 10. In particular, there is no contact between the rod 608 and the surface 226 of the dispense interface 200. Accordingly, the spring 602 is relaxed and the push rod 601 is hold in a first position in the drug delivery device 10. In this first position of the push rod 601 in the drug delivery device 10, the first switch 603 and the second switch 604 face the set back parallel surface portion 605 and the spring 602, respectively. In particular, there is no contact between the lateral surface of the push rod 601 and the first switch 603 and the second switch 604. Both switches are deactivated.

In FIG. 12b, attaching of the dispense interface 200 to the drug delivery device 10 is initiated such that the dispense interface 200 is aligned to the distal end 42 of the cartridge holder 40 and pushed towards the drug delivery device 10 to axially slid over the distal end 42 of the cartridge housing 40 of the drug delivery device 10. Thereby, the distal end of the rod 608 resides on the surface 226 of the dispense interface 200 and is also pushed towards the drug delivery device 10 such that, during attaching the dispense interface 200 to the drug delivery device 10, the movement of the dispense interface 200 towards the drug delivery device facilitates a corresponding movement of the push rod 601 and a compression of the spring 602.

When the push rod 601 is correspondingly moved, the first switch 603 and the second switch 604 slide along the inclined surface portion 607 of the lateral surface of the push rod 601 towards the parallel surface portion 606 and, thereby, increasing pressure is applied on the switches. When a pressure threshold is overcome, the first switch 603 and the second switch 604 are activated, for instance, the switches are activated, when residing on the parallel surface portion 606 (i.e. an activating portion of the push rod).

Due to its distal position, the first switch 603 resides on the parallel surface portion 606 before the second switch 604 resides thereon and is, thus, earlier activated. When the attaching is initiated as illustrated in FIG. 12b, the first switch 603 resides on the parallel surface portion 606 and is activated.

In FIG. 12c, attaching of the dispense interface 200 to the drug delivery device 10 is completed such that the dispense interface resides in fluid communication with the primary medicament 92 of the first cartridge 90 and the secondary medicament 102 of the second cartridge 100. Furthermore, the protruding members of the cartridge housing (e.g. protruding member 48) may cooperate with the first and second recess 217, 219 of the dispense interface 200 to form a secured mechanical connection such as a snap lock.

When the attaching of the dispense interface 200 to the drug delivery device 10 is completed as illustrated in FIG. 12c, the second switch 604 also resides on the parallel surface portion 606 and is activated. The spring 602 is compressed and the push rod is in a second position.

In this position the dispense interface 200 is considered as completely attached to the cartridge housing 40 and a timer for measuring the life time of the dispense interface 200 can be started.

When the dispense interface 200 is released from the drug delivery device 10, the compressed spring 602 relaxes and moves the push rod 601 back to the first position and optionally the dispense interface 200 to a detent position (i.e. the position illustrated in FIG. 12b). Thereby, firstly the second switch 604 and then the first switch 603 slide along the inclined surface portion 607 towards the set back parallel surface 605 and are subsequently deactivated.

When the first and/or the second switch are deactivated, to completely remove the dispense interface and be forced to attach a new dispense interface 200.

FIG. 13 illustrates a functional block diagram of a control unit to operate and control the drug delivery device illustrated in FIG. 1. FIG. 14 illustrates one arrangement of a printed circuit board (PCB) or printed circuit board assembly (PCBA) 350 that may comprise certain portions of the control unit illustrated in FIG. 13. The components described in the following can also be provided by separate circuit boards.

Referring now to both FIGS. 13 and 14, it may be seen that the control unit 300 comprises a microcontroller 302. The microcontroller is used to control the electronic system for the drug delivery device 10.

The control unit further comprises a power management module 304 coupled to the microcontroller 302 and other circuit elements. The power management module 304 receives a supply voltage from a main power source such as the battery 306 and regulates this supply voltage to a plurality of voltages required by other circuit components of the control unit 300.

The battery 306 provides power to the control unit 300 and is preferably supplied by a single lithium-ion or lithium-polymer cell. This cell may be encapsulated in a battery pack that contains safety circuitry to protect against overheating, overcharging and excessive discharge. A battery charger 308 may be coupled to the battery 306.

Preferably, the control unit further comprises a plurality of switches 316. In the illustrated arrangement, the control unit 300 may comprise two switches 316 and these switches may be distributed around the device. These switches 316 may be used to detect and/or confirm in particular whether the dispense interface 200 has been properly attached to the drug delivery device 10. Such switches are exemplarily illustrated in FIG. 11. There may further be additional switches in order to detect and/or confirm whether the removable cap 18 has been properly attached to the main body 20 of the drug delivery device 10, whether the first cartridge retainer 50 of the cartridge holder 40 for the first cartridge 90 has been properly closed, whether the second cartridge retainer 52 of the cartridge holder 40 for the second cartridge 100 has been properly closed, or to detect the presence of the first cartridge 90 and/or of the second cartridge 100.

In order to detect whether the dispense interface 200 has been properly attached to the drug delivery device 10, there may alternatively or additionally to the switches also be provided further sensors, for example a light barrier, a camera, a barcode reader, a proximity sensor or the like.

These switches and/or sensors 316 are connected to digital inputs, for example to general purpose digital inputs, on the microcontroller 302. Preferably, these digital inputs may be multiplexed in order to reduce the number of input lines required. Interrupt lines may also be used appropriately on the microcontroller 302 so as to ensure timely response to changes in switch status.

In addition, and as described in greater detail above, the control unit may also be operatively coupled to a plurality of human interface elements or push buttons 318. In one preferred arrangement, the control unit 300 comprises eight push buttons 318 and these are used on the device for user input for different user input functions.

These buttons 318 are connected to digital inputs, for example to general purpose digital inputs, on the microcontroller. Again, these digital inputs may be multiplexed so as to reduce the number of input lines required. Interrupt lines will be used appropriately on the microcontroller to ensure timely response to changes in switch status. In an example embodiment, the function of one or more buttons may be replaced by a touch screen.

In addition, the control unit 300 comprises a real time clock 320. The real-time clock 320 may communicate with the microcontroller 302 using a serial peripheral interface or similar. The real time clock may be used as a timer in order to determine the end of life of the dispense interface, for example. For this, the time when the dispense interface 200 is attached to the medical device 10 is saved, for example in the memory device 324. The difference between the current time and the saved time yields the time period of attachment of the dispense interface. The real time clock can alternatively be integrated into the microcontroller 302. This further saves space and components for realizing a timer to measure life time of a dispense assembly.

A digital display module 322 in the device preferably uses LCD or OLED technology and provides a visual signal to the user, for example of the display 80. The display module incorporates the display itself and a display driver integrated circuit. This circuit communicates with the microcontroller 302 using a serial peripheral interface or parallel bus. The end of life of the dispense interface 200 can be indicated over the display. The user can also be requested to remove the current dispense interface 200 or attach a new dispense interface 200.

As previously mentioned, a sounder 330 may also be provided in the drug delivery device 10. The proposed sounder may be used to provide an audible signal to the user. Instead of or additional to the visual indication relating to the end of life of the dispense interface, audible information may be provided for the same reason.

The control unit 300 further comprises a first motor driver 332 and a second motor driver 334. For example, where the motor drive comprises a stepper motor drive, the drive may be controlled using general purpose digital outputs. Alternatively, where the motor drive comprises a brushless DC motor drive, the drive may be controlled using a Pulse Width Modulated (PWM) digital output. These signals control a power stage, which switches current through the motor windings. The power stage requires continuous electrical commutation. This may for example increase device safety, decreasing the probability of erroneous drug delivery.

The motor drivers 332, 334 may also be controlled by a separate motor drive microcontroller (not shown) being in communication with the microcontroller 302.

The power stage may consist of a dual H-bridge per stepper motor, or three half-bridges per brushless DC motor. These may be implemented using either discrete semiconductor parts or monolithic integrated circuits.

The control unit 300 further comprises a first and a second motor 336, 338, respectively. The first motor 336 may be used to move the stopper (not shown) in the first cartridge 90. Similarly, the second motor 338 may be used to move the stopper (not shown) in the second cartridge. The motors can be stepper motors, brushless DC motors, or any other type of electric motor. The type of motor may determine the type of motor drive circuit used. The electronics for the device may be implemented with one main, rigid printed circuit board assembly, potentially with additional smaller flexible sections as required, e.g., for connection to motor windings and switches.

In order to prevent usage of the device, the microprocessor 302 can prevent usage of the device 10 by not allowing signals to be sent to the motor drivers 332, 334, for instance. In this way, the device is still usable for other actions than dispensing.

Figure 15:
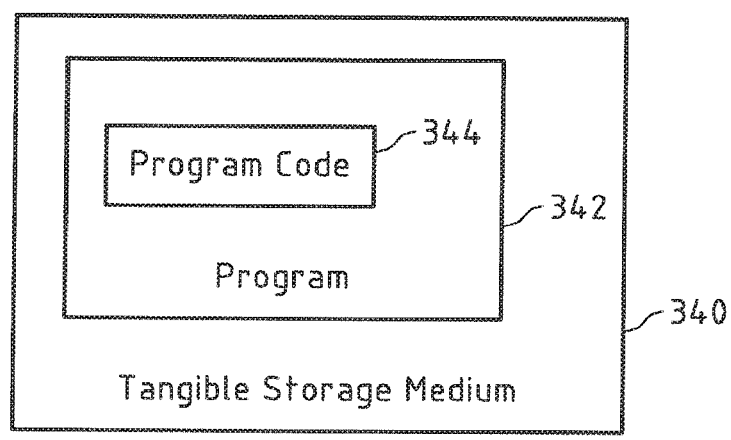
FIG. 15 schematically illustrates an exemplary embodiment of a tangible storage medium according to the present invention.

FIG. 15 schematically illustrates an exemplary embodiment of a tangible storage medium 340 according to the present invention. Tangible storage medium 340 may for instance store a computer program 342, with program code 344 for detecting an attachment of a dispense assembly to a medical device, in particular a medical device according to the invention, determining whether the end of life of the dispense interface is reached and indicating the end of life of the dispense assembly. Tangible storage medium 340 is a readably medium, for instance a computer-readable or processor-readable medium. Accordingly, the computer program 342 stored on tangible storage medium 340 may be executable by a computer or a processor. Tangible storage medium 340 may for instance be embodied as an electric, magnetic, electro-magnetic, optic or other tangible storage medium, and may either be a removable medium or a medium that is fixedly installed in an apparatus or device, such as for instance medical device 10 of FIG. 1.

Figure 16:
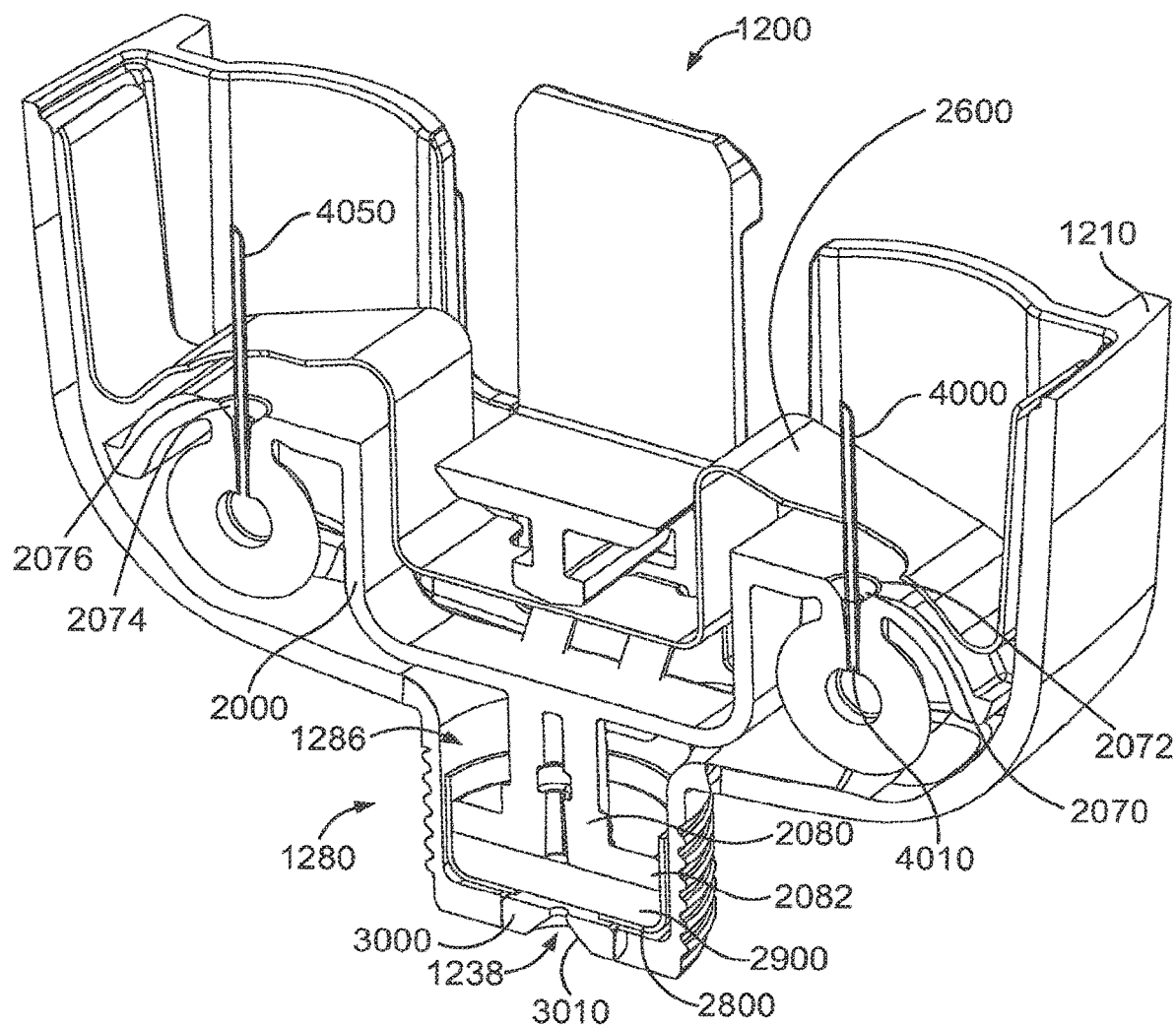
FIG. 16 illustrates a cross sectional view of the another exemplary embodiment of a dispense interface with a mechanical lock-out mechanism.

FIG. 16 shows a cross section of another embodiment of a dispense interface 1200. The dispense interface may as well be adapted such that it actuates the sensors discussed in connection with dispense interface 200.

Figure 17:
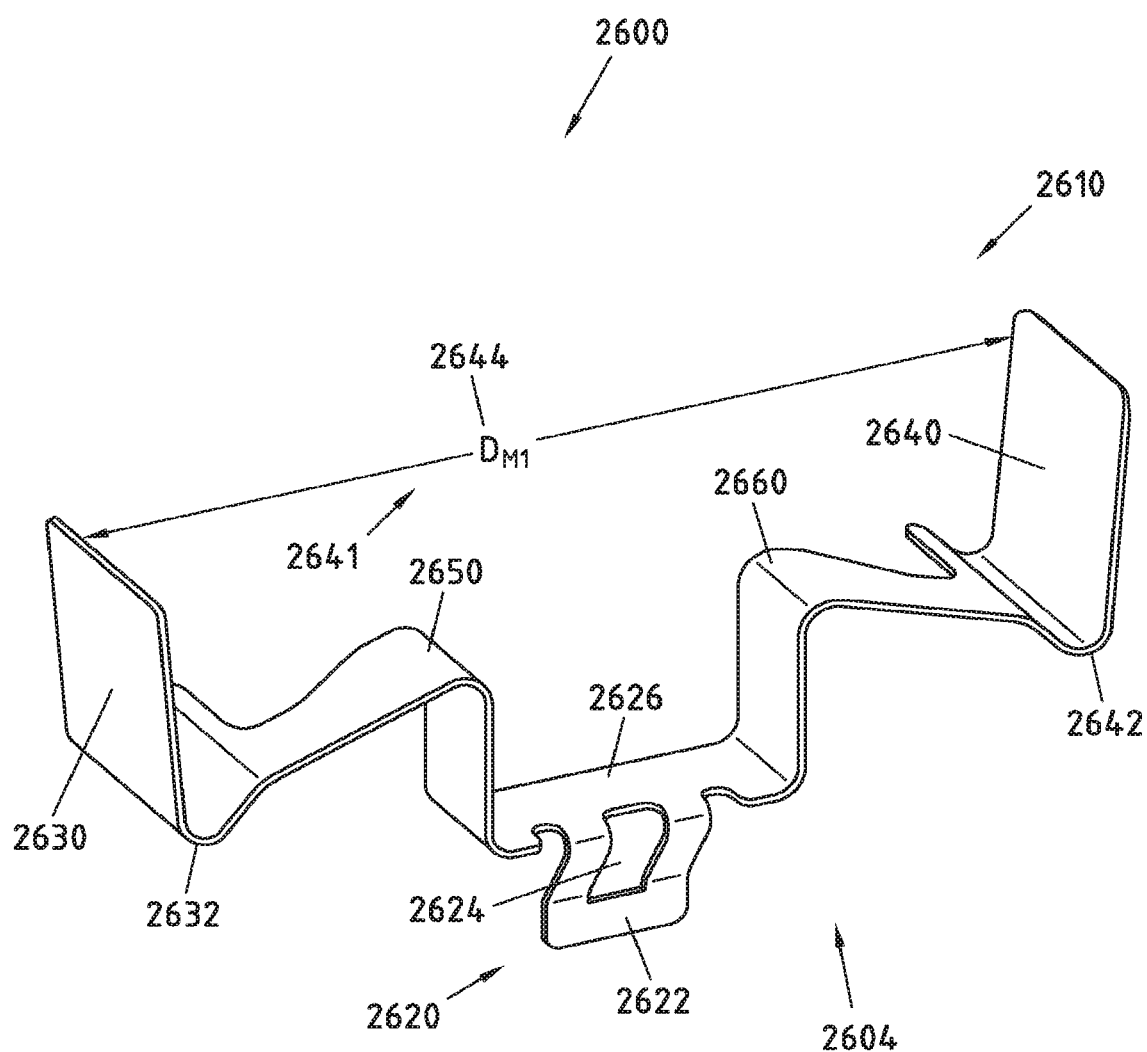
FIG. 17 illustrates a perspective view of a lock-out spring of the dispense interface illustrated in FIG. 16.

As may be seen from FIG. 16, the dispense interface 1200 further comprises a mechanical lock-out mechanism in form of dispense interface lockout member in the form of a lockout spring 2600. FIG. 17 illustrates a perspective view of such one arrangement of such a lock out member 2600 in an initial, unbiased or unstressed state. One reason that a lock out member may be incorporated into a dispense interface, such as the interface 200 illustrated in FIG. 1, is to ensure that once the dispense interface is removed from the drug delivery device, the dispense interface cannot be re-attached and used a second time. Preventing re-attachment tends to ensure that medicament is not allowed to reside in the dispense interface 1200 indefinitely and contaminate the drug delivered to the patient. This is particularly advantageous in combination with a life time limitation of the dispense interface.

In the illustrated arrangement in FIGS. 16 and 17, the lock out spring resides in a first or an initial position. As illustrated, the lock out spring 2600 extends from a distal spring end 2604 to a proximal spring end 2620. Near its distal end 2604, the lock out spring 2600 comprises a spring tip 2620. This spring tip 2620 comprises a tab 2622 defining a recess 2624.

Near its proximal end 2610, the lock out spring 2600 comprises a first spring arm 2630 and a second spring arm 2340. For example, the first spring arm 2630 extends proximally from a first pivot point 2632 of the spring 2632. Similarly, the second spring arm 2340 extends proximally from a second pivot point 2642 of the spring 2600. In the initial spring position illustrated in FIG. 16, both the first and the second spring arms 2630, 2640 reside in an unstressed state. That is, both arms flex radially outward, away from one another a spaced amount defining an initial distance DM1 2644 (cf. FIG. 17) of a mouth created between the first and the second spring arm 2630, 2640. When the spring 2600 is placed within a stressed state (so as to lock out the spring preventing re-attachment), the first and second spring arms 2630, 2640 flex towards one another at the first and second pivot points 2632, 2642, respectively. This flexing causes the arms 2630, 2640 to reduce the initial distance DM1 of the mouth to a smaller second mouth distance DM2.

Figure 18:
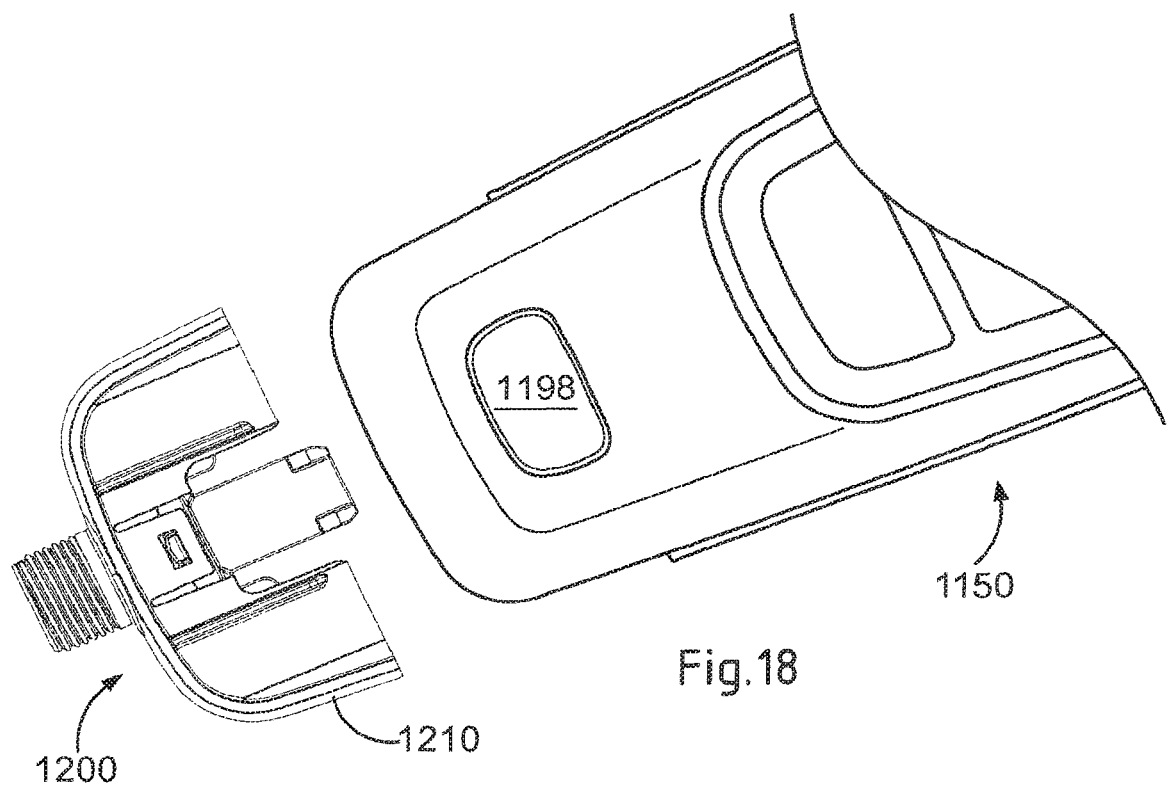
FIG. 18 illustrates a perspective view of the dispense interface illustrated in FIG. 16 about to be mounted onto a drug delivery device.

FIG. 18 illustrates the dispense interface 1200 illustrated in FIG. 16 about to be mounted onto a distal end of a drug delivery device, such as the drug delivery device 1150 in FIG. 18. In this pre-attachment illustration, the lock out spring contained within the dispense interface 1200 resides in the first or initial position, as illustrated in FIG. 16.

Figure 19:
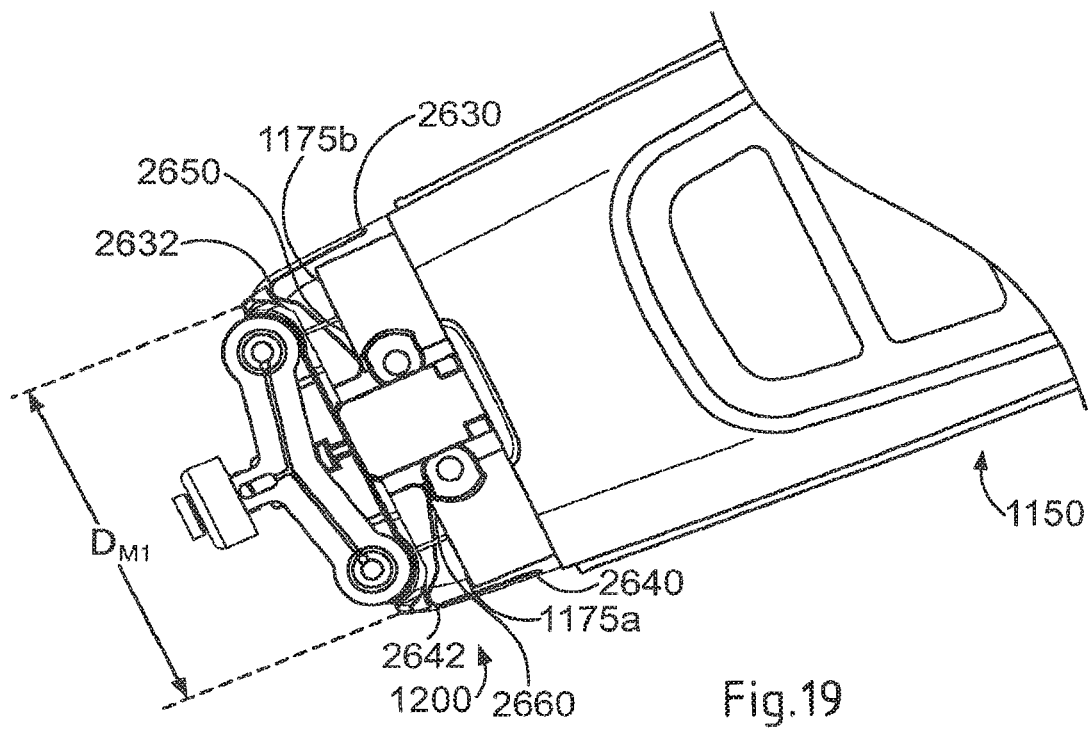
FIG. 19 illustrates a perspective view of the dispense interface illustrated in FIG. 16 in a partially seated position onto a drug delivery device.

FIG. 19 illustrates the dispense interface 1200 illustrated in FIG. 18 after the dispense interface has been moved to a first attached position. For ease of explanation, certain component parts of the dispense interface 1200 have been removed, such as the outer body 1210, so that the various configurations of the lock out spring may be illustrated and/or explained. For example, in this illustrated initial attached position, the outer body 1210 of the dispense interface 1200 has been removed so as to illustrate the lock out spring 2600 and how it changes state during attachment of the dispense interface to the drug delivery device 1150. As illustrated, both the first and the second spring knuckles 2650, 2660 have entered the distal end 1152 of the drug delivery device and have made contact with a face of the cartridge holder. For example, the first spring knuckle 2650 has made contact with a first cartridge holder face 1175b and the second spring knuckle 2660 has made contact with a second cartridge holder face 1175a. As also illustrated, both the first and second lock out spring arms 2630, 2640 have entered the distal end of the drug delivery device and reside between the outer body of the device and the cartridge holders. However, as the dispense interface continues to move in the proximal direction from this initial illustrated position, the cartridge holder faces 1175 a,b begin to exert pressure on the first and second spring knuckles 2650, 2660. This exerted pressure tends to bend the first and second spring arms 2630, 2640 inwardly, towards one another so as to reduce the initial diameter DM1 of mouth.

Once the proximal end of the dispense interface 1200 enters the distal end of the drug delivery device 1150, when mounted onto the inner body 2000 of the dispense interface, the spring tip 2620 will be mounted on a retention rib provided on the inner body 2000. For example, FIG. 19 shows the lock out spring 2600 mounted on the inner body 2000 in a first or initial position. In this initial position, the spring tip 2620 resides over the retention rib 2090 on the inner body 2000. In addition, a bottom flat surface 2622 of the spring tip 2620 resides adjacent a flat distal surface of the first outer protrusion 2006 of the inner body 2000.

When in this initial condition, the arms of the spring are disposed to flex outwards, away from the center of the spring assembly. As such, as the dispense interface 1200 is fitted onto the distal end of the drug delivery device, the distal face of the device pushes on the lock out spring 2600, forcing the spring to move in the distal direction. This axial movement of the spring 2600 causes the spring to flex about its spring arms 2630, 2640. As these arms are restrained from rotating by the presence of the cartridge doors of the drug delivery device, the spring slides in the distal direction. This distal movement occurs until the spring tip 2622 snaps over the retention rib 2090 on the inner body 2000.

Figure 20:
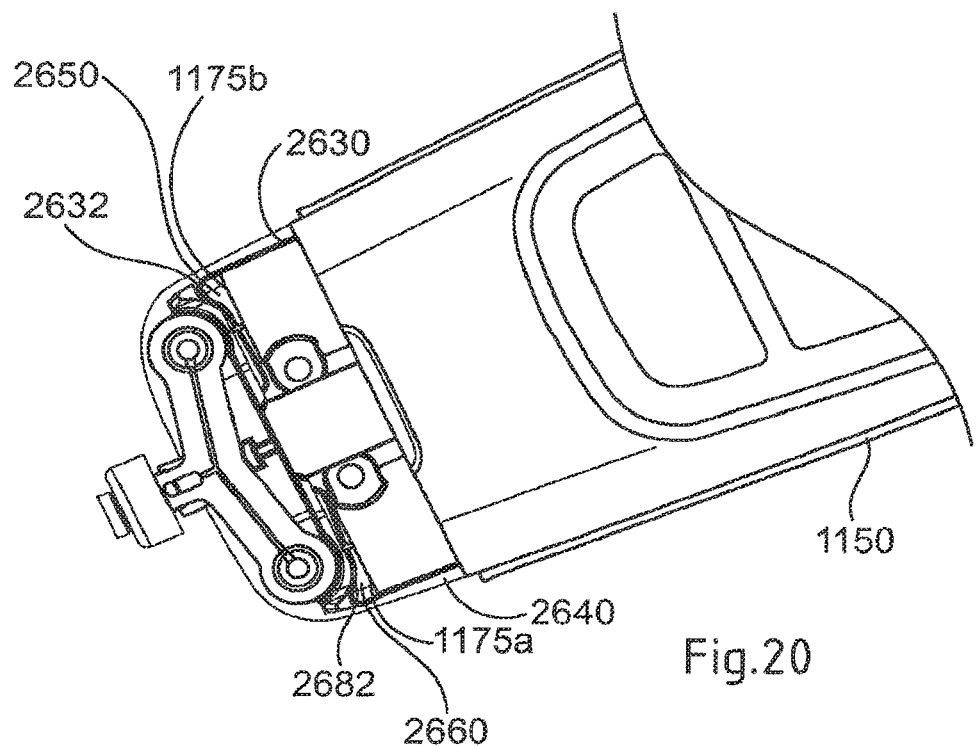
FIG. 20 illustrates a perspective view of the dispense interface illustrated in FIG. 16 in a fully seated position on a drug delivery device.

FIG. 20 illustrates the dispense interface 1200 illustrated in FIG. 19 in a fully seated position. As illustrated, in this fully seated position, both the first and second spring arms 2630, 2640 now reside along an outer surface of the cartridge holders and thereby exert an inwardly directed pressure against these cartridge holders. In addition, the first spring portion residing between first pivot point 2632 and the first knuckle 2650 flattens out along the first cartridge holder face 1175b. Similarly, the second spring portion residing between the second pivot point and the second knuckle 2660 also flattens out along the second cartridge holder face 1175a. Once the spring tip 2620 has snapped over the retention tip 2090 of the inner body 2000, the spring tip 2620 cannot be easily retracted in the proximal direction so as to allow the spring tip 2620 to move back over the retention rib 2090. As such, a spring force is built up in the first and second spring arms 2630, 2640 as they are forced against the cartridge holder until such a time as the dispense interface is removed from the device.

Figure 21:
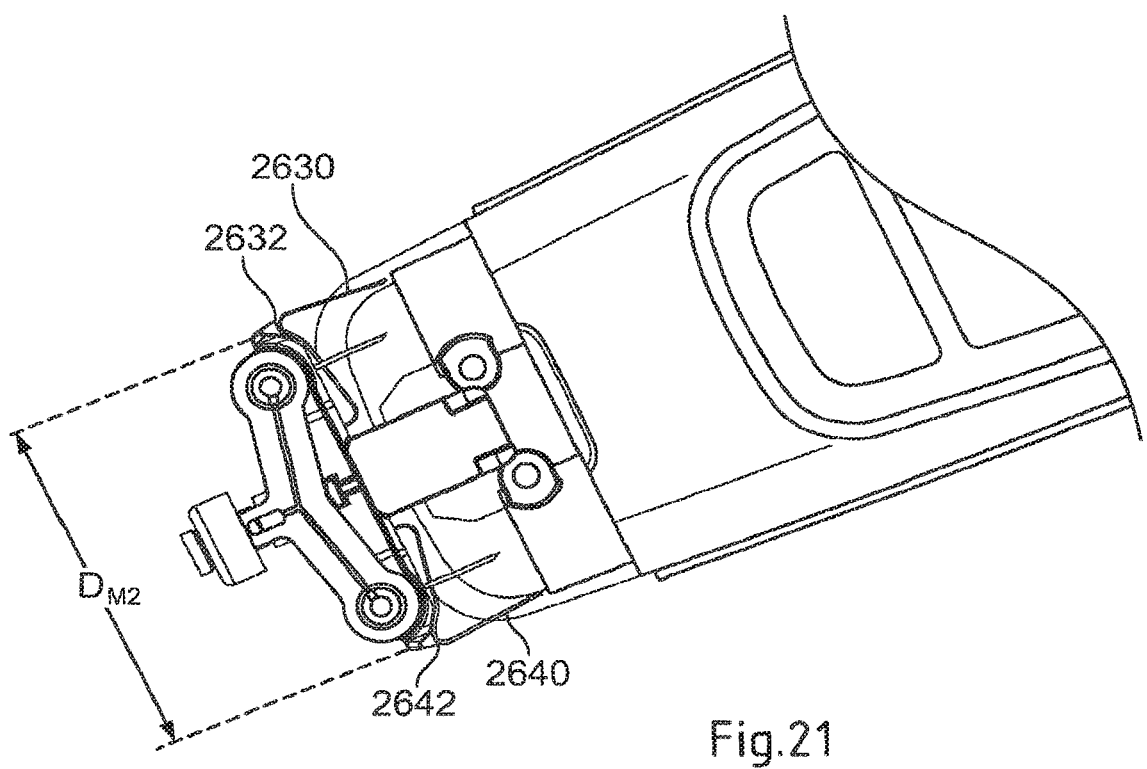
FIG. 21 illustrates a perspective view of the dispense interface illustrated in FIG. 16 in a partially removed position from a drug delivery device.

A release button (not shown) on the drug delivery device may be pushed or manually activated to as to allow the user to remove the attached dispense interface 1200. FIG. 21 illustrates the dispense interface 1200 in a first position as it is being removed from the distal end of the drug delivery device 1150. As the dispense interface 1200 is removed from the device, the distal ends of the cartridge doors move out of engagement with the inwardly biased first and second spring arms 2630, 2640. As such, both spring arms 2630, 2640 are able to rotate as they relax and flex back towards one another.

Once the spring arms 2630, 2640 of the spring 2600 have rotated, they reside in an interference position which is illustrated in FIG. 21. For example, in this interference position, if one were to try to reattach the dispense interface 1200 onto the drug delivery device 1150, the spring arms 2630, 2640 would interfere with the distal end of the cartridge holders of the drug delivery device since these arms are no longer spaced apart the larger mouth distance DM1 as illustrated in FIG. 19 but are spaced apart a smaller mouth distance DM2. As such, the dispense interface 1200 is prevented from being reattached to the drug delivery device and thereby locks out or prevents the dispense interface 1200 from further attachment. The shape of the inner body 2000 and the support it gives to the spring help to ensure that the lock out spring 2600 cannot be easily forced or pushed out of the way by a user attempting to refit the dispense interface back onto the drug delivery device.

Figure 22:
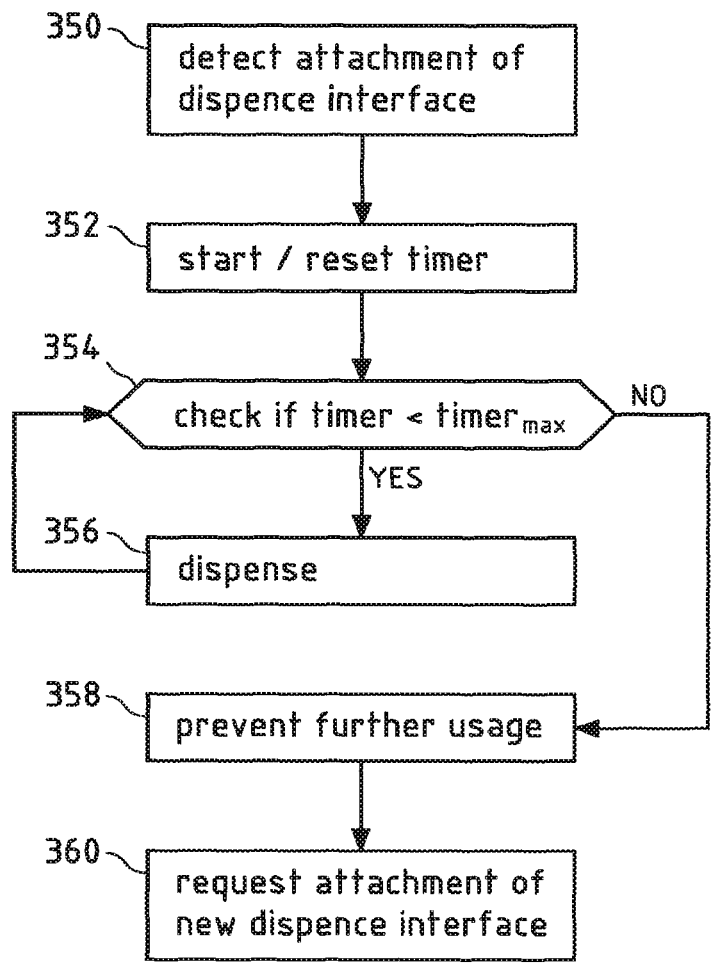
FIG. 22 illustrates in a flow chart an exemplary embodiment of a method according to the invention.

FIG. 22 illustrates in a flow chart an exemplary embodiment of a method according to the invention. In step 350 the attachment of the dispense interface to the medical device is detected. This can be realized by the sensors 43, 43a and/or 43b for example. When the corresponding sensor sends a signal the control unit, for example the micro-controller 302, a timer is started. In case the timer was already running because of an earlier attached dispense interface or assembly, the timer is reset.

The steps 354 and 356 now illustrate the behavior of exemplary embodiment of a medical device according to the invention during the use of the device for dispensing one or two medicaments. Each time the user requests a dose to be dispensed, the micro-controller checks in step 354 whether the timer is still less than a maximum allowed period of life time "timermax" for the attached dispense interface, in order to determine whether the end of life of the dispense interface is reached or has already been reached. It is additionally or alternatively conceivable that this criterion is checked regularly, independent of the use of the device or the dispense of the medicament. In case the timer is still less than the maximum allowed time, the dispense of the medicaments can be performed in step 356. The user can continue to use the same dispense interface as long as the timer is less than the maximum allowed time.

In case the timer is not less than the maximum allowed time, the medical device prevents further usage of the device in step 358, since it can not be guaranteed that the remaining fluids in the dispense interface are harmless for the user. Preventing further usage can mean to only prevent any further dispense of the medicaments. It can also mean that the user is prevented from any further input to the device.

Over a display the detachment of the dispense interface is the requested from the user in step 360. It is possible to reset the timer when the sensors detect detachment of the dispense interface. It is also possible to keep the timer running and reset the timer in step 352.

When the user has detached the used dispense interface and attaches a new dispense interface, the method will start again with step 350.

The term "drug" or "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exedin-3 or exedin-4 or an analogue or derivative of exedin-3 or exedin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyhepta-idecanoyl) human insulin.

Exendin-4 for example means Exendin-4(1-39), a peptide of the sequence H His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:
H-(Lys)4-des Pro36, des Pro37 Exendin-4(1-39)-NH2,
H-(Lys)5-des Pro36, des Pro37 Exendin-4(1-39)-NH2,
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;
or an Exendin-4 derivative of the sequence
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2, H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2) 25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2) 25, Asp28] Exendin-4(1-39)-(Lys)6-NH2;
or a pharmaceutically acceptable salt or solvate of any one of the afore-mentioned Exedin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region (CH) and the variable region (VH). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1 C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

What is claimed is:

1. A drug delivery device configured to deliver at least one medicament, the drug delivery device comprising:
    a main body;
    a cartridge retainer configured to receive a cartridge of a medicament, the cartridge retainer including a hinged connection to the main body and being moveable between an open position and a closed position;
    one or more first sensors configured to detect the presence of the cartridge in the cartridge retainer, wherein the one or more first sensors are pressure activated switches; and
    one or more second sensors configured to detect that the cartridge retainer is in the closed position, wherein the one or more second sensors are selected from the group of sensors consisting of a light barrier sensor, a camera, a barcode reader, and a proximity sensor.

2. The drug delivery device according to claim 1, wherein the drug delivery device further comprises a controller including the one or more first sensors.

3. The drug delivery device according to claim 2, wherein the one or more first sensors are each connected to digital inputs of the controller.

4. The drug delivery device according to claim 2, wherein the controller is configured to control at least one motor drive for expulsion of the medicament from the cartridge.

5. The drug delivery device according to claim 4, wherein the at least one motor drive is a stepper motor.

6. The drug delivery device according to claim 2, wherein the controller is operatively coupled to a plurality of human interface elements or push buttons.

7. The drug delivery device according to claim 2, further comprising a display, wherein the controller is configured to provide device information to the display.

8. The drug delivery device according to claim 7, wherein the device information includes information regarding the medicament contained within the cartridge.

9. The drug delivery device according to claim 7, wherein the display comprises a liquid crystal display (LCD) or an organic light emitting diode display (OLED).

10. The drug delivery device according to claim 1, further comprising a second cartridge retainer configured to receive a second cartridge of a second medicament, the second cartridge retainer comprising a second hinged connection to the main body and being moveable between an open position and a closed position.

11. A system comprising:
    a replaceable cartridge containing a medicament; and
    a drug delivery device configured to deliver at least one medicament, the drug delivery device comprising:
        a main body;
        a cartridge retainer configured to receive the replaceable cartridge of the medicament, the cartridge retainer including a hinged connection to the main body and being moveable between an open position and a closed position;
        one or more first sensors configured to detect the presence of the replaceable cartridge in the cartridge retainer, wherein the one or more first sensors are pressure activated switches; and
        one or more second sensors configured to detect that the cartridge retainer is in the closed position, wherein the one or more second sensors are selected from the group of sensors consisting of a light barrier sensor, a camera, a barcode reader, and a proximity sensor.

12. A method of detecting the presence of a cartridge of a medicament in a cartridge retainer of a drug delivery device, the method comprising:
    providing the drug delivery device including:
        a main body;
        the cartridge retainer configured to receive the cartridge of medicament, the cartridge retainer including a hinged connection to the main body and being moveable between an open position and a closed position; and
        a controller including:
            one or more first sensors configured to detect the presence of the cartridge in the cartridge retainer, wherein the one or more first sensors are pressure activated switches; and one or more second sensors configured to detect that the cartridge retainer is in the closed position, wherein the one or more second sensors are selected from the group of sensors consisting of a light barrier sensor, a camera, a barcode reader, and a proximity sensor;

the controller receiving signals from the one or more first sensors and the one or more second sensors via digital inputs of the controller; and the controller determining from the received signals whether the cartridge is present in the cartridge retainer and whether the cartridge retainer is in the closed position.

* * * * *

SEQUENCE LISTING

```
<160> NUMBER OF SEQ ID NOS: 1

<210> SEQ ID NO 1
<211> LENGTH: 39
<212> TYPE: PRT
<213> ORGANISM: Artificial Sequence
<220> FEATURE:
<223> OTHER INFORMATION: Synthetic

<400> SEQUENCE: 1

Ser Pro Pro Pro Ala Gly Ser Ser Pro Gly Gly Asn Lys Leu Trp Glu
1               5                   10                  15

Ile Phe Leu Arg Val Ala Glu Glu Glu Met Gln Lys Ser Leu Asp Ser
            20                  25                  30

Thr Phe Thr Gly Glu Gly His
            35
```